United States Patent
Gupta et al.

(10) Patent No.: US 11,823,295 B2
(45) Date of Patent: Nov. 21, 2023

(54) SYSTEMS AND METHODS FOR REDUCING RISK OF PATHOGEN EXPOSURE WITHIN A SPACE

(71) Applicant: Honeywell International Inc., Morris Plains, NJ (US)

(72) Inventors: Bhavesh Gupta, Niantic, CT (US); Prabhat Ranjan, Bangalore (IN)

(73) Assignee: HONEYWELL INTERNATIONAL, INC., Charlotte, NC (US)

( * ) Notice: Subject to any disclaimer, the term of this patent is extended or adjusted under 35 U.S.C. 154(b) by 269 days.

(21) Appl. No.: 16/907,018

(22) Filed: Jun. 19, 2020

(65) Prior Publication Data
US 2021/0398230 A1     Dec. 23, 2021

(51) Int. Cl.
*F24F 11/52*     (2018.01)
*G06Q 50/16*     (2012.01)
(Continued)

(52) U.S. Cl.
CPC ............. *G06Q 50/163* (2013.01); *A61L 2/10* (2013.01); *A61L 2/24* (2013.01); *A61L 2/26* (2013.01);
(Continued)

(58) Field of Classification Search
CPC ...... G06Q 50/163; G06Q 50/12; G16H 40/67; G16H 40/20; G16H 50/30; G16H 50/20;
(Continued)

(56) References Cited

U.S. PATENT DOCUMENTS

| 191,512 A | 6/1877 | Bennett et al. |
|---|---|---|
| 4,009,647 A | 3/1977 | Howorth |

(Continued)

FOREIGN PATENT DOCUMENTS

| CA | 2387100 A1 | 11/2003 |
|---|---|---|
| CA | 2538139 A1 | 3/2005 |

(Continued)

OTHER PUBLICATIONS

Ijaz, M. Khalid, Zargar, Bahram, Wright, K.E., Rubino, J.R. and Sattar, S.A., 2016. Generic aspects of the airborne spread of human pathogens indoors and emerging air decontamination technologies. American Journal of Infection Control, 44(9), pp. S109-S120. (Year: 2016).*

(Continued)

*Primary Examiner* — Alicia M. Choi
(74) *Attorney, Agent, or Firm* — Seager, Tufte & Wickhem, LLP

(57) ABSTRACT

A system reduces risk of pathogen exposure within a space that is located within a facility having a plurality of spaces that periodically have one or more people within the space. The system includes one or more occupancy sensors that are configured to provide an indication of when the space is occupied and when the space is not occupied. A sanitizer is configured to sanitize surfaces within the space when activated. A controller is operably coupled with the one or more occupancy sensors and the sanitizer. The controller is configured to determine a designated time to sanitize the space based at least in part upon information received from the one or more occupancy sensors and to automatically instruct the sanitizer to sanitize surfaces within the space at the designated time.

19 Claims, 5 Drawing Sheets

(51) Int. Cl.

| | |
|---|---|
| *G16H 40/67* | (2018.01) |
| *G16H 40/20* | (2018.01) |
| *G16H 50/30* | (2018.01) |
| *A61L 2/10* | (2006.01) |
| *A61L 2/24* | (2006.01) |
| *A61L 2/26* | (2006.01) |
| *A61L 9/20* | (2006.01) |
| *G05B 13/02* | (2006.01) |
| *G06Q 50/12* | (2012.01) |
| *G07C 9/00* | (2020.01) |
| *F24F 8/00* | (2021.01) |
| *F24F 110/50* | (2018.01) |
| *G16H 50/20* | (2018.01) |
| *G16H 50/80* | (2018.01) |
| *F24F 11/00* | (2018.01) |

(52) U.S. Cl.
CPC ............ *A61L 9/20* (2013.01); *F24F 8/00* (2021.01); *F24F 11/52* (2018.01); *G05B 13/0265* (2013.01); *G06Q 50/12* (2013.01); *G07C 9/00* (2013.01); *G16H 40/20* (2018.01); *G16H 40/67* (2018.01); *G16H 50/30* (2018.01); *A61L 2202/11* (2013.01); *A61L 2202/14* (2013.01); *A61L 2202/25* (2013.01); *A61L 2209/111* (2013.01); *A61L 2209/16* (2013.01); *F24F 11/00* (2013.01); *F24F 2110/50* (2018.01); *G16H 50/20* (2018.01); *G16H 50/80* (2018.01)

(58) Field of Classification Search
CPC ... G16H 50/80; F24F 11/52; F24F 8/00; F24F 2110/50; F24F 11/00; F24F 11/30; A61L 2/10; A61L 2/24; A61L 2/26; A61L 9/20; A61L 2202/11; A61L 2202/14; A61L 2202/25; A61L 2209/111; A61L 2209/16; G05B 13/0265; G07C 9/00; Y02B 30/70
See application file for complete search history.

(56) References Cited

U.S. PATENT DOCUMENTS

| | | | |
|---|---|---|---|
| 4,375,637 A | 3/1983 | Desjardins | |
| 4,918,615 A | 4/1990 | Suzuki et al. | |
| 4,939,922 A | 7/1990 | Smalley et al. | |
| 5,566,084 A | 10/1996 | Cmar | |
| 5,727,579 A | 3/1998 | Chardack | |
| 5,745,126 A | 4/1998 | Jain et al. | |
| 5,751,916 A | 5/1998 | Kon et al. | |
| 5,777,598 A | 7/1998 | Gowda et al. | |
| 5,973,662 A | 10/1999 | Singers et al. | |
| 6,065,842 A | 5/2000 | Fink | |
| 6,139,177 A | 10/2000 | Venkatraman et al. | |
| 6,144,993 A | 11/2000 | Fukunaga et al. | |
| 6,157,943 A | 12/2000 | Meyer | |
| 6,229,429 B1 | 5/2001 | Horon | |
| 6,238,337 B1 | 5/2001 | Kambhatla et al. | |
| 6,334,211 B1 | 12/2001 | Kojima et al. | |
| 6,353,853 B1 | 3/2002 | Gravlin | |
| 6,369,695 B2 | 4/2002 | Horon | |
| 6,375,038 B1 | 4/2002 | Daansen et al. | |
| 6,429,868 B1 | 8/2002 | Dehner, Jr. et al. | |
| 6,473,084 B1 | 10/2002 | Phillips et al. | |
| 6,487,457 B1 | 11/2002 | Hull et al. | |
| 6,580,950 B1 | 6/2003 | Johnson et al. | |
| 6,598,056 B1 | 7/2003 | Hull et al. | |
| 6,619,555 B2 | 9/2003 | Rosen | |
| 6,704,012 B1 | 3/2004 | Lefave | |
| 6,720,874 B2 | 4/2004 | Fufido et al. | |
| 6,741,915 B2 | 5/2004 | Poth | |
| 6,796,896 B2 | 9/2004 | Laiti | |
| 6,801,199 B1 | 10/2004 | Wallman | |
| 6,816,878 B1 | 11/2004 | Zimmers et al. | |
| 6,876,951 B2 | 4/2005 | Skidmore et al. | |
| 6,882,278 B2 | 4/2005 | Winings et al. | |
| 6,904,385 B1 | 6/2005 | Budike, Jr. | |
| 6,907,387 B1 | 6/2005 | Reardon | |
| 6,911,177 B2 | 6/2005 | Deal | |
| 6,993,403 B1 | 1/2006 | Dadebo et al. | |
| 6,993,417 B2 | 1/2006 | Osann, Jr. | |
| 7,023,440 B1 | 4/2006 | Havekost et al. | |
| 7,031,880 B1 | 4/2006 | Seem et al. | |
| 7,062,722 B1 | 6/2006 | Carlin et al. | |
| 7,110,843 B2 | 9/2006 | Pagnano et al. | |
| 7,139,685 B2 | 11/2006 | Bascle et al. | |
| 7,164,972 B2 | 1/2007 | Imhof et al. | |
| 7,183,899 B2 | 2/2007 | Behnke | |
| 7,200,639 B1 | 4/2007 | Yoshida | |
| 7,222,111 B1 | 5/2007 | Budike, Jr. | |
| 7,222,800 B2 | 5/2007 | Wruck | |
| 7,257,397 B2 | 8/2007 | Shamoon et al. | |
| 7,280,030 B1 | 10/2007 | Monaco | |
| 7,292,908 B2 | 11/2007 | Borne et al. | |
| 7,295,116 B2 | 11/2007 | Kumar et al. | |
| 7,302,313 B2 | 11/2007 | Sharp et al. | |
| 7,308,323 B2 | 12/2007 | Kruk et al. | |
| 7,308,388 B2 | 12/2007 | Beverina et al. | |
| 7,313,447 B2 | 12/2007 | Hsiung et al. | |
| 7,346,433 B2 | 3/2008 | Budike, Jr. | |
| 7,356,548 B1 | 4/2008 | Culp et al. | |
| 7,379,782 B1 | 5/2008 | Cocco | |
| 7,383,148 B2 | 6/2008 | Ahmed | |
| 7,434,742 B2 | 10/2008 | Mueller et al. | |
| 7,447,333 B1 | 11/2008 | Masticola et al. | |
| 7,466,224 B2 | 12/2008 | Ward et al. | |
| 7,496,472 B2 | 2/2009 | Seem | |
| 7,512,450 B2 | 3/2009 | Ahmed | |
| 7,516,490 B2 | 4/2009 | Riordan et al. | |
| 7,548,833 B2 | 6/2009 | Ahmed | |
| 7,551,092 B1 | 6/2009 | Henry | |
| 7,557,729 B2 | 7/2009 | Hubbard et al. | |
| 7,567,844 B2 | 7/2009 | Thomas et al. | |
| 7,596,473 B2 | 9/2009 | Hansen et al. | |
| 7,610,910 B2 | 11/2009 | Ahmed | |
| 7,626,507 B2 | 12/2009 | LaCasse | |
| 7,664,574 B2 | 2/2010 | Imhof et al. | |
| 7,682,464 B2 | 3/2010 | Glenn et al. | |
| 7,702,421 B2 | 4/2010 | Sullivan et al. | |
| 7,729,882 B2 | 6/2010 | Seem | |
| 7,755,494 B2 | 7/2010 | Melker et al. | |
| 7,761,310 B2 | 7/2010 | Rodgers | |
| 7,774,227 B2 | 8/2010 | Srivastava | |
| 7,788,189 B2 * | 8/2010 | Budike, Jr. | H02J 13/00028 700/83 |
| 7,797,188 B2 | 9/2010 | Srivastava | |
| 7,819,136 B1 | 10/2010 | Eddy | |
| 7,822,806 B2 | 10/2010 | Frank et al. | |
| 7,856,370 B2 | 12/2010 | Katta et al. | |
| 7,978,083 B2 | 7/2011 | Melker et al. | |
| 7,984,384 B2 | 7/2011 | Chaudhri et al. | |
| 7,986,323 B2 | 7/2011 | Kobayashi et al. | |
| 8,024,666 B2 | 9/2011 | Thompson | |
| 8,086,047 B2 | 12/2011 | Penke et al. | |
| 8,099,178 B2 | 1/2012 | Mairs et al. | |
| 8,151,280 B2 | 4/2012 | Sather et al. | |
| 8,176,095 B2 | 5/2012 | Murray et al. | |
| 8,218,871 B2 | 7/2012 | Angell et al. | |
| 8,219,660 B2 | 7/2012 | McCoy et al. | |
| 8,271,941 B2 | 9/2012 | Zhang et al. | |
| 8,294,585 B2 | 10/2012 | Barnhill | |
| 8,302,020 B2 | 10/2012 | Louch et al. | |
| 8,320,634 B2 | 11/2012 | Deutsch | |
| 8,334,422 B2 | 12/2012 | Gutsol et al. | |
| 8,344,893 B1 | 1/2013 | Drammeh | |
| 8,375,118 B2 | 2/2013 | Hao et al. | |
| 8,473,080 B2 | 6/2013 | Seem et al. | |
| 8,476,590 B2 | 7/2013 | Stratmann et al. | |
| 8,516,016 B2 | 8/2013 | Park et al. | |
| 8,558,660 B2 | 10/2013 | Nix et al. | |
| 8,639,527 B2 | 1/2014 | Rensvold et al. | |
| 8,698,637 B2 | 4/2014 | Raichman | |

(56) References Cited

U.S. PATENT DOCUMENTS

| | | | |
|---|---|---|---|
| 8,816,860 | B2 | 8/2014 | Ophardt et al. |
| 8,869,027 | B2 | 10/2014 | Louch et al. |
| 8,904,497 | B2 | 12/2014 | Hsieh |
| 8,936,944 | B2 | 1/2015 | Peltz et al. |
| 8,947,437 | B2 | 2/2015 | Garr et al. |
| 8,950,019 | B2 | 2/2015 | Loberger et al. |
| 9,000,926 | B2 | 4/2015 | Hollock et al. |
| 9,002,532 | B2 | 4/2015 | Asmus |
| 9,030,325 | B2 | 5/2015 | Taneff |
| 9,098,738 | B2 | 8/2015 | Bilet et al. |
| 9,105,071 | B2 | 8/2015 | Fletcher et al. |
| 9,175,356 | B2 | 11/2015 | Peltz et al. |
| 9,235,657 | B1 | 1/2016 | Wenzel et al. |
| 9,240,111 | B2 | 1/2016 | Scott et al. |
| 9,256,702 | B2 | 2/2016 | Elbsat et al. |
| 9,280,884 | B1 | 3/2016 | Schultz et al. |
| 9,292,972 | B2 | 3/2016 | Hailemariam et al. |
| 9,320,662 | B2 | 4/2016 | Hayes et al. |
| 9,322,566 | B2 | 4/2016 | Wenzel et al. |
| 9,355,069 | B2 | 5/2016 | Elbsat et al. |
| 9,370,600 | B1 | 6/2016 | DuPuis et al. |
| 9,373,242 | B1 | 6/2016 | Conrad et al. |
| 9,396,638 | B2 | 7/2016 | Wildman et al. |
| 9,311,807 | B2 | 8/2016 | Schultz et al. |
| 9,406,212 | B2 | 8/2016 | De Luca et al. |
| 9,418,535 | B1 | 8/2016 | Felch et al. |
| 9,418,536 | B1 | 8/2016 | Felch et al. |
| 9,436,179 | B1 | 9/2016 | Turney et al. |
| 9,447,985 | B2 | 9/2016 | Johnson, Jr. |
| 9,449,219 | B2 | 9/2016 | Bilet et al. |
| 9,477,543 | B2 | 10/2016 | Henley et al. |
| 9,497,832 | B2 | 11/2016 | Verberkt et al. |
| 9,513,364 | B2 | 12/2016 | Hall et al. |
| 9,526,380 | B2 | 12/2016 | Hamilton et al. |
| 9,526,806 | B2 | 12/2016 | Park et al. |
| 9,536,415 | B2 | 1/2017 | De Luca et al. |
| 9,558,648 | B2 | 1/2017 | Douglas |
| 9,568,204 | B2 | 2/2017 | Asmus et al. |
| 9,581,985 | B2 | 2/2017 | Walser et al. |
| 9,591,267 | B2 | 3/2017 | Lipton et al. |
| 9,606,520 | B2 | 3/2017 | Noboa et al. |
| 9,612,601 | B2 | 4/2017 | Beyhaghi et al. |
| 9,613,518 | B2 | 4/2017 | Dunn et al. |
| 9,618,224 | B2 | 4/2017 | Emmons et al. |
| 9,640,059 | B2 | 5/2017 | Hyland |
| 9,672,360 | B2 | 6/2017 | Barkan |
| 9,696,054 | B2 | 7/2017 | Asmus |
| 9,710,700 | B2 | 7/2017 | Bilet et al. |
| 9,715,242 | B2 | 7/2017 | Pillai et al. |
| 9,721,452 | B2 | 8/2017 | Felch et al. |
| 9,729,945 | B2 | 8/2017 | Schultz et al. |
| 9,778,639 | B2 | 10/2017 | Boettcher et al. |
| 9,784,464 | B2 | 10/2017 | Yamamoto et al. |
| 9,798,336 | B2 | 10/2017 | Przybylski |
| 9,843,743 | B2 | 12/2017 | Lewis et al. |
| 9,852,481 | B1 | 12/2017 | Turney et al. |
| 9,856,634 | B2 | 1/2018 | Rodenbeck et al. |
| 9,857,301 | B1 * | 1/2018 | Nourbakhsh ........ G01N 33/007 |
| 9,872,088 | B2 | 1/2018 | Fadell et al. |
| 9,875,639 | B2 | 1/2018 | Bone et al. |
| 9,911,312 | B2 | 3/2018 | Wildman et al. |
| 9,940,819 | B2 | 4/2018 | Ferniany |
| 9,956,306 | B2 | 5/2018 | Brais et al. |
| 9,982,903 | B1 | 5/2018 | Ridder et al. |
| 9,986,175 | B2 | 5/2018 | Frank et al. |
| 10,007,259 | B2 | 6/2018 | Turney et al. |
| 10,055,114 | B2 | 8/2018 | Shah et al. |
| 10,087,608 | B2 | 10/2018 | Dobizl et al. |
| 10,101,730 | B2 | 10/2018 | Wenzel et al. |
| 10,101,731 | B2 | 10/2018 | Asmus et al. |
| 10,156,554 | B1 * | 12/2018 | Hoff ................... G01N 33/0062 |
| 10,175,681 | B2 | 1/2019 | Wenzel et al. |
| 10,222,083 | B2 | 3/2019 | Drees et al. |
| 10,223,894 | B2 | 3/2019 | Raichman |
| 10,228,837 | B2 | 3/2019 | Hua et al. |
| 10,235,865 | B2 | 3/2019 | Thyroff |
| 10,251,610 | B2 | 4/2019 | Parthasarathy et al. |
| 10,282,796 | B2 | 5/2019 | Elbsat et al. |
| 10,288,306 | B2 | 5/2019 | Ridder et al. |
| 10,303,843 | B2 | 5/2019 | Bitran et al. |
| 10,317,864 | B2 | 6/2019 | Boettcher et al. |
| 10,332,382 | B2 | 6/2019 | Thyroff |
| 10,359,748 | B2 | 7/2019 | Elbsat et al. |
| 10,386,820 | B2 | 8/2019 | Wenzel et al. |
| 10,402,767 | B2 | 9/2019 | Noboa et al. |
| 10,514,178 | B2 | 12/2019 | Willmott et al. |
| 10,514,817 | B2 | 12/2019 | Hua et al. |
| 10,520,210 | B2 | 12/2019 | Park et al. |
| 10,544,955 | B2 | 1/2020 | Przybylski |
| 10,558,178 | B2 | 2/2020 | Willmott et al. |
| 10,559,180 | B2 | 2/2020 | Pourmohammad et al. |
| 10,559,181 | B2 | 2/2020 | Pourmohammad et al. |
| 10,565,844 | B2 | 2/2020 | Pourmohammad et al. |
| 10,600,263 | B2 | 3/2020 | Park et al. |
| 10,602,474 | B2 | 3/2020 | Goldstein |
| 10,605,477 | B2 | 3/2020 | Ridder |
| 10,607,147 | B2 | 3/2020 | Raykov et al. |
| 10,619,882 | B2 | 4/2020 | Chatterjee et al. |
| 10,627,124 | B2 | 4/2020 | Walser et al. |
| 10,673,380 | B2 | 6/2020 | Wenzel et al. |
| 10,678,227 | B2 | 6/2020 | Przybylski et al. |
| 10,706,375 | B2 | 7/2020 | Wenzel et al. |
| 10,726,711 | B2 | 7/2020 | Subramanian et al. |
| 10,732,584 | B2 | 8/2020 | Elbsat et al. |
| 10,767,885 | B2 | 9/2020 | Przybylski et al. |
| 10,775,988 | B2 | 9/2020 | Narain et al. |
| 10,796,554 | B2 | 10/2020 | Vincent et al. |
| 10,809,682 | B2 | 10/2020 | Patil et al. |
| 10,809,705 | B2 | 10/2020 | Przybylski |
| 10,824,125 | B2 | 11/2020 | Elbsat et al. |
| 10,854,194 | B2 | 12/2020 | Park et al. |
| 10,871,298 | B2 | 12/2020 | Ridder et al. |
| 10,871,756 | B2 † | 12/2020 | Johnson |
| 10,876,754 | B2 | 12/2020 | Wenzel et al. |
| 10,890,904 | B2 | 1/2021 | Turney et al. |
| 10,900,686 | B2 | 1/2021 | Willmott et al. |
| 10,901,446 | B2 | 1/2021 | Nesler et al. |
| 10,908,578 | B2 | 2/2021 | Johnson, Jr. et al. |
| 10,909,642 | B2 | 2/2021 | Elbsat et al. |
| 10,915,094 | B2 | 2/2021 | Wenzel et al. |
| 10,917,740 | B1 | 2/2021 | Scott et al. |
| 10,921,768 | B2 | 2/2021 | Johnson, Jr. et al. |
| 10,921,972 | B2 | 2/2021 | Park et al. |
| 10,921,973 | B2 | 2/2021 | Park et al. |
| 10,928,790 | B2 | 2/2021 | Mueller et al. |
| 10,948,884 | B2 | 3/2021 | Beaty et al. |
| 10,949,777 | B2 | 3/2021 | Elbsat et al. |
| 10,955,800 | B2 | 3/2021 | Burroughs et al. |
| 10,956,842 | B2 | 3/2021 | Wenzel et al. |
| 10,962,945 | B2 | 3/2021 | Park et al. |
| 10,969,135 | B2 | 4/2021 | Willmott et al. |
| 11,002,457 | B2 | 5/2021 | Turney et al. |
| 11,009,252 | B2 | 5/2021 | Turney et al. |
| 11,010,846 | B2 | 5/2021 | Elbsat et al. |
| 11,016,648 | B2 | 5/2021 | Fala et al. |
| 11,016,998 | B2 | 5/2021 | Park et al. |
| 11,022,947 | B2 | 6/2021 | Elbsat et al. |
| 11,024,292 | B2 | 6/2021 | Park et al. |
| 11,036,249 | B2 | 6/2021 | Elbsat |
| 11,038,709 | B2 | 6/2021 | Park et al. |
| 11,042,139 | B2 | 6/2021 | Deshpande et al. |
| 11,042,924 | B2 | 6/2021 | Asmus et al. |
| 11,061,424 | B2 | 7/2021 | Elbsat et al. |
| 11,068,821 | B2 | 7/2021 | Wenzel et al. |
| 11,070,389 | B2 | 7/2021 | Schuster et al. |
| 11,073,976 | B2 | 7/2021 | Park et al. |
| 11,080,289 | B2 | 8/2021 | Park et al. |
| 11,080,426 | B2 | 8/2021 | Park et al. |
| 11,086,276 | B2 | 8/2021 | Wenzel et al. |
| 11,094,186 | B2 | 8/2021 | Razak |
| 11,108,587 | B2 | 8/2021 | Park et al. |
| 11,131,473 | B2 | 8/2021 | Risbeck et al. |
| 11,113,295 | B2 | 9/2021 | Park et al. |
| 11,119,458 | B2 | 9/2021 | Asp et al. |

(56) References Cited

U.S. PATENT DOCUMENTS

| | | |
|---|---|---|
| 11,120,012 B2 | 9/2021 | Park et al. |
| 11,150,617 B2 | 10/2021 | Ploegert et al. |
| 11,151,983 B2 | 10/2021 | Park et al. |
| 11,156,978 B2 | 10/2021 | Johnson, Jr. et al. |
| 11,156,996 B2 | 10/2021 | Schuster et al. |
| 11,158,306 B2 | 10/2021 | Park et al. |
| 11,182,047 B2 | 11/2021 | Nayak et al. |
| 11,188,093 B2 | 11/2021 | Ko et al. |
| 11,195,401 B2 | 12/2021 | Pourmohammad |
| 11,217,087 B2 | 1/2022 | Pelski |
| 11,226,126 B2 | 1/2022 | Przybylski et al. |
| 11,243,523 B2 | 2/2022 | Llopis et al. |
| 11,268,715 B2 | 3/2022 | Park et al. |
| 11,268,996 B2 | 3/2022 | Vitullo et al. |
| 11,269,505 B2 | 3/2022 | Fala et al. |
| 11,272,011 B1 | 3/2022 | Laughton et al. |
| 11,272,316 B2 | 3/2022 | Scott et al. |
| 11,275,348 B2 | 3/2022 | Park et al. |
| 11,275,363 B2 | 3/2022 | Przybylski et al. |
| 11,281,169 B2 | 3/2022 | Chatterjee et al. |
| 11,288,754 B2 | 3/2022 | Elbsat et al. |
| 11,314,726 B2 | 4/2022 | Park et al. |
| 11,314,788 B2 | 4/2022 | Park et al. |
| 11,334,044 B2 | 5/2022 | Goyal |
| 11,353,834 B2 | 6/2022 | Mueller et al. |
| 11,356,292 B2 | 6/2022 | Ploegert et al. |
| 11,360,451 B2 | 6/2022 | Pancholi et al. |
| 11,361,123 B2 | 6/2022 | Ploegert et al. |
| 2002/0111698 A1 | 8/2002 | Graziano et al. |
| 2002/0130868 A1 | 9/2002 | Smith |
| 2003/0028269 A1 | 2/2003 | Spriggs et al. |
| 2003/0030637 A1 | 2/2003 | Grinstein et al. |
| 2003/0046862 A1 | 3/2003 | Wolf et al. |
| 2003/0071814 A1 | 4/2003 | Jou et al. |
| 2003/0078677 A1 | 4/2003 | Hull et al. |
| 2003/0083957 A1 | 5/2003 | Olefson |
| 2003/0103075 A1 | 6/2003 | Rosselot |
| 2003/0171851 A1 | 9/2003 | Brickfield et al. |
| 2003/0214400 A1 | 11/2003 | Mizutani et al. |
| 2003/0217143 A1 * | 11/2003 | Dudley ............... F24F 11/52 709/224 |
| 2003/0233432 A1 | 12/2003 | Davis et al. |
| 2004/0001009 A1 | 1/2004 | Winings et al. |
| 2004/0064260 A1 | 4/2004 | Padmanabhan et al. |
| 2004/0143474 A1 | 7/2004 | Haeberle et al. |
| 2004/0153437 A1 | 8/2004 | Buchan |
| 2004/0168115 A1 | 8/2004 | Bauernschmidt et al. |
| 2004/0233192 A1 | 11/2004 | Hopper |
| 2004/0260411 A1 | 12/2004 | Cannon |
| 2005/0010460 A1 | 1/2005 | Mizoguchi et al. |
| 2005/0040943 A1 * | 2/2005 | Winick ............... F24F 11/56 340/539.1 |
| 2005/0119767 A1 | 6/2005 | Kiwimagi et al. |
| 2005/0143863 A1 | 6/2005 | Ruane et al. |
| 2005/0267900 A1 | 12/2005 | Ahmed et al. |
| 2006/0004841 A1 | 1/2006 | Heikkonen et al. |
| 2006/0009862 A1 | 1/2006 | Imhof et al. |
| 2006/0017547 A1 | 1/2006 | Buckingham et al. |
| 2006/0020177 A1 | 1/2006 | Seo et al. |
| 2006/0028471 A1 | 2/2006 | Kincaid et al. |
| 2006/0029256 A1 | 2/2006 | Miyoshi et al. |
| 2006/0058900 A1 | 3/2006 | Johanson et al. |
| 2006/0067545 A1 | 3/2006 | Lewis et al. |
| 2006/0067546 A1 | 3/2006 | Lewis et al. |
| 2006/0077255 A1 | 4/2006 | Cheng |
| 2006/0184326 A1 | 8/2006 | McNally et al. |
| 2006/0231568 A1 | 10/2006 | Lynn et al. |
| 2006/0247826 A1 * | 11/2006 | Green ............... F24F 11/38 700/276 |
| 2006/0265664 A1 | 11/2006 | Simons et al. |
| 2006/0279630 A1 | 12/2006 | Aggarwal et al. |
| 2007/0016955 A1 | 1/2007 | Goldberg et al. |
| 2007/0055757 A1 | 3/2007 | Mairs et al. |
| 2007/0055760 A1 | 3/2007 | McCoy et al. |
| 2007/0061046 A1 | 3/2007 | Mairs et al. |
| 2007/0067062 A1 | 3/2007 | Mairs et al. |
| 2007/0088534 A1 | 4/2007 | MacArthur et al. |
| 2007/0090951 A1 | 4/2007 | Chan et al. |
| 2007/0091091 A1 | 4/2007 | Gardiner et al. |
| 2007/0101433 A1 | 5/2007 | Louch et al. |
| 2007/0114295 A1 | 5/2007 | Jenkins |
| 2007/0120652 A1 | 5/2007 | Behnke |
| 2007/0139208 A1 | 6/2007 | Kates |
| 2007/0216682 A1 | 9/2007 | Navratil et al. |
| 2007/0219645 A1 | 9/2007 | Thomas et al. |
| 2007/0239484 A1 | 10/2007 | Arond et al. |
| 2007/0268122 A1 | 11/2007 | Kow et al. |
| 2008/0001763 A1 | 1/2008 | Raja et al. |
| 2008/0027885 A1 | 1/2008 | Van Putten et al. |
| 2008/0036593 A1 | 2/2008 | Rose-Pehrsson et al. |
| 2008/0062167 A1 | 3/2008 | Boggs et al. |
| 2008/0099045 A1 | 5/2008 | Glenn et al. |
| 2008/0103798 A1 | 5/2008 | Domenikos et al. |
| 2008/0120396 A1 | 5/2008 | Jayaram et al. |
| 2008/0144885 A1 | 6/2008 | Zucherman et al. |
| 2008/0183424 A1 | 7/2008 | Seem |
| 2008/0194009 A1 | 8/2008 | Marentis |
| 2008/0198231 A1 | 8/2008 | Ozdemir et al. |
| 2008/0209342 A1 | 8/2008 | Taylor et al. |
| 2008/0222565 A1 | 9/2008 | Taylor et al. |
| 2008/0224862 A1 | 9/2008 | Cirker |
| 2008/0242945 A1 | 10/2008 | Gugliotti et al. |
| 2008/0250800 A1 | 10/2008 | Wetzel |
| 2008/0279420 A1 | 11/2008 | Masticola et al. |
| 2008/0280275 A1 | 11/2008 | Collopy |
| 2008/0303658 A1 | 12/2008 | Melker et al. |
| 2008/0306985 A1 | 12/2008 | Murray et al. |
| 2008/0320552 A1 | 12/2008 | Kumar et al. |
| 2009/0001181 A1 | 1/2009 | Siddaramanna et al. |
| 2009/0024944 A1 | 1/2009 | Louch et al. |
| 2009/0065596 A1 | 3/2009 | Seem et al. |
| 2009/0083120 A1 | 3/2009 | Strichman et al. |
| 2009/0096791 A1 | 4/2009 | Abshear et al. |
| 2009/0125337 A1 | 5/2009 | Abri |
| 2009/0125825 A1 | 5/2009 | Rye et al. |
| 2009/0144023 A1 | 6/2009 | Seem |
| 2009/0157744 A1 | 6/2009 | McConnell |
| 2009/0160673 A1 | 6/2009 | Cirker |
| 2009/0322782 A1 | 12/2009 | Kimchi et al. |
| 2010/0048167 A1 | 2/2010 | Chow et al. |
| 2010/0058248 A1 | 3/2010 | Park |
| 2010/0064001 A1 | 3/2010 | Daily |
| 2010/0070089 A1 | 3/2010 | Harrod et al. |
| 2010/0073162 A1 | 3/2010 | Johnson et al. |
| 2010/0123560 A1 | 5/2010 | Nix et al. |
| 2010/0134296 A1 | 6/2010 | Hwang |
| 2010/0156628 A1 | 6/2010 | Ainsbury et al. |
| 2010/0156630 A1 | 6/2010 | Ainsbury |
| 2010/0188228 A1 | 7/2010 | Hyland |
| 2010/0223198 A1 | 9/2010 | Noureldin et al. |
| 2010/0249955 A1 | 9/2010 | Sitton |
| 2010/0286937 A1 | 11/2010 | Hedley et al. |
| 2010/0318200 A1 | 12/2010 | Foslien et al. |
| 2010/0324962 A1 | 12/2010 | Nesler et al. |
| 2011/0010654 A1 | 1/2011 | Raymond et al. |
| 2011/0057799 A1 | 3/2011 | Taneff |
| 2011/0077779 A1 | 3/2011 | Fuller et al. |
| 2011/0083094 A1 * | 4/2011 | Laycock ............... F24F 11/30 715/772 |
| 2011/0087988 A1 | 4/2011 | Ray et al. |
| 2011/0112854 A1 | 5/2011 | Koch et al. |
| 2011/0126111 A1 | 5/2011 | Gill et al. |
| 2011/0154426 A1 | 6/2011 | Doser et al. |
| 2011/0161124 A1 | 6/2011 | Lappinga et al. |
| 2011/0169646 A1 | 7/2011 | Raichman |
| 2011/0184563 A1 | 7/2011 | Foslien et al. |
| 2011/0202467 A1 | 8/2011 | Hilber et al. |
| 2011/0273298 A1 | 11/2011 | Snodgrass et al. |
| 2011/0291841 A1 | 12/2011 | Hollock et al. |
| 2011/0298301 A1 | 12/2011 | Wong et al. |
| 2011/0316703 A1 | 12/2011 | Butler et al. |
| 2011/0320054 A1 | 12/2011 | Brzezowski |
| 2012/0022700 A1 | 1/2012 | Drees et al. |
| 2012/0039503 A1 | 2/2012 | Chen et al. |

(56) References Cited

U.S. PATENT DOCUMENTS

| | | |
|---|---|---|
| 2012/0062382 A1 | 3/2012 | Taneff |
| 2012/0075464 A1 | 3/2012 | Derenne et al. |
| 2012/0109988 A1 | 5/2012 | Li et al. |
| 2012/0112883 A1 | 5/2012 | Wallace et al. |
| 2012/0131217 A1 | 5/2012 | Delorme et al. |
| 2012/0158185 A1 | 6/2012 | El-Mankabady et al. |
| 2012/0216243 A1 | 8/2012 | Gill et al. |
| 2012/0224057 A1 | 9/2012 | Gill et al. |
| 2012/0259466 A1 | 10/2012 | Ray et al. |
| 2012/0262472 A1 | 10/2012 | Garr et al. |
| 2012/0272146 A1 | 10/2012 | D'souza et al. |
| 2012/0291068 A1 | 11/2012 | Khushoo et al. |
| 2012/0303652 A1 | 11/2012 | Tseng |
| 2012/0310418 A1 | 12/2012 | Harrod et al. |
| 2013/0055132 A1 | 2/2013 | Foslien |
| 2013/0060794 A1 | 3/2013 | Puttabasappa et al. |
| 2013/0082842 A1 | 4/2013 | Balazs et al. |
| 2013/0086152 A1 | 4/2013 | Hersche et al. |
| 2013/0091631 A1 | 4/2013 | Hayes et al. |
| 2013/0110295 A1 | 5/2013 | Zheng et al. |
| 2013/0169681 A1 | 7/2013 | Rasane et al. |
| 2013/0184880 A1 | 7/2013 | McMahon |
| 2013/0187775 A1 | 7/2013 | Marsden et al. |
| 2013/0204570 A1 | 8/2013 | Mendelson et al. |
| 2013/0229276 A1 | 9/2013 | Hunter |
| 2013/0268293 A1 | 10/2013 | Knudson et al. |
| 2013/0289774 A1 | 10/2013 | Day et al. |
| 2014/0032157 A1 | 1/2014 | Khiani |
| 2014/0040998 A1 | 2/2014 | Hsieh |
| 2014/0046490 A1 | 2/2014 | Foslien et al. |
| 2014/0046722 A1 | 2/2014 | Rosenbloom et al. |
| 2014/0058539 A1 | 2/2014 | Park |
| 2014/0167917 A2 | 6/2014 | Wallace et al. |
| 2014/0207289 A1* | 7/2014 | Golden .................. F24F 11/52 715/771 |
| 2014/0207291 A1 | 7/2014 | Golden et al. |
| 2014/0292518 A1 | 10/2014 | Wildman et al. |
| 2014/0307076 A1 | 10/2014 | Deutsch |
| 2014/0309757 A1 | 10/2014 | Le Sant et al. |
| 2014/0316582 A1 | 10/2014 | Berg-Sonne et al. |
| 2014/0320289 A1 | 10/2014 | Raichman |
| 2014/0342724 A1 | 11/2014 | Hill et al. |
| 2015/0025329 A1 | 1/2015 | Amarasingham et al. |
| 2015/0032264 A1 | 1/2015 | Emmons et al. |
| 2015/0056909 A1 | 2/2015 | Chien |
| 2015/0070174 A1 | 3/2015 | Douglas |
| 2015/0077258 A1 | 3/2015 | Nelson et al. |
| 2015/0113462 A1 | 4/2015 | Chen et al. |
| 2015/0153918 A1 | 6/2015 | Chen et al. |
| 2015/0161874 A1 | 6/2015 | Thyroff et al. |
| 2015/0167995 A1 | 6/2015 | Fadell et al. |
| 2015/0168949 A1 | 6/2015 | Hua et al. |
| 2015/0194043 A1 | 7/2015 | Dunn et al. |
| 2015/0198707 A1 | 7/2015 | Al-Alusi |
| 2015/0212717 A1 | 7/2015 | Nair et al. |
| 2015/0213222 A1 | 7/2015 | Amarasingham et al. |
| 2015/0213379 A1 | 7/2015 | Nair et al. |
| 2015/0216369 A1 | 8/2015 | Hamilton et al. |
| 2015/0253748 A1 | 9/2015 | Brun et al. |
| 2015/0281287 A1 | 10/2015 | Gill et al. |
| 2016/0061473 A1 | 3/2016 | Johnson, Jr. |
| 2016/0061476 A1 | 3/2016 | Schultz et al. |
| 2016/0061477 A1 | 3/2016 | Schultz et al. |
| 2016/0061794 A1 | 3/2016 | Schultz et al. |
| 2016/0061795 A1 | 3/2016 | Schultz et al. |
| 2016/0063833 A1 | 3/2016 | Schultz et al. |
| 2016/0066067 A1 | 3/2016 | Schultz et al. |
| 2016/0116181 A1* | 4/2016 | Aultman .................. F24F 11/62 700/276 |
| 2016/0139067 A1 | 5/2016 | Grace |
| 2016/0253897 A1 | 9/2016 | Wildman et al. |
| 2016/0255516 A1 | 9/2016 | Hill et al. |
| 2016/0298864 A1 | 10/2016 | Ekolind et al. |
| 2016/0306934 A1 | 10/2016 | Sperry et al. |
| 2016/0314683 A1 | 10/2016 | Felch et al. |
| 2016/0328948 A1 | 11/2016 | Ferniany |
| 2016/0335731 A1 | 11/2016 | Hall |
| 2016/0367925 A1 | 12/2016 | Blackley |
| 2017/0024986 A1 | 1/2017 | Austin |
| 2017/0193792 A1 | 7/2017 | Bermudez Rodriguez et al. |
| 2017/0256155 A1 | 9/2017 | Sengstaken, Jr. |
| 2017/0280949 A1 | 10/2017 | Wildman et al. |
| 2017/0294106 A1 | 10/2017 | Thyroff |
| 2017/0365024 A1 | 12/2017 | Koch et al. |
| 2018/0016773 A1 | 1/2018 | Chandler et al. |
| 2018/0073759 A1* | 3/2018 | Zhang .................. F24F 11/30 |
| 2018/0119973 A1* | 5/2018 | Rothman .................. F24F 11/62 |
| 2018/0151054 A1 | 5/2018 | Pi |
| 2018/0218591 A1 | 8/2018 | Easter |
| 2018/0259927 A1 | 9/2018 | Przybylski et al. |
| 2018/0293038 A1 | 10/2018 | Meruva et al. |
| 2018/0301014 A1 | 10/2018 | Worral et al. |
| 2018/0313695 A1 | 11/2018 | Shim et al. |
| 2018/0365957 A1 | 12/2018 | Wright et al. |
| 2019/0051138 A1 | 2/2019 | Easter |
| 2019/0139395 A1 | 5/2019 | Rogachev et al. |
| 2019/0209719 A1 | 7/2019 | Andersen et al. |
| 2019/0277530 A1* | 9/2019 | Schwegler .................. F24F 11/56 |
| 2020/0003448 A1* | 1/2020 | Schwegler .................. F24F 11/39 |
| 2020/0009280 A1 | 1/2020 | Kupa et al. |
| 2020/0074836 A1 | 3/2020 | Kolavennu et al. |
| 2020/0090089 A1 | 3/2020 | Aston et al. |
| 2020/0146442 A1* | 5/2020 | Rutzke .................. A47B 21/04 |
| 2020/0146557 A1 | 5/2020 | Cheung et al. |
| 2020/0196812 A1* | 6/2020 | Takayanagi .................. G01V 8/10 |
| 2020/0200420 A1 | 6/2020 | Nayak et al. |
| 2020/0256571 A1 | 8/2020 | Johnson, Jr. et al. |
| 2021/0010701 A1 | 1/2021 | Suindykov et al. |
| 2021/0011443 A1 | 1/2021 | Mcnamara et al. |
| 2021/0011444 A1 | 1/2021 | Risbeck et al. |
| 2021/0071886 A1* | 3/2021 | Gillette .................. F24F 11/32 |
| 2021/0356927 A1 | 11/2021 | Johnson, Jr. et al. |
| 2021/0364181 A1 | 11/2021 | Risbeck et al. |
| 2021/0373519 A1* | 12/2021 | Risbeck .................. F24F 11/64 |
| 2021/0379524 A1* | 12/2021 | Prigge .................. F24F 11/61 |
| 2022/0011731 A1 | 1/2022 | Risbeck et al. |
| 2022/0042694 A1* | 2/2022 | He .................. F24F 11/88 |
| 2022/0113045 A1 | 4/2022 | Gamroth et al. |
| 2022/0137580 A1 | 5/2022 | Burroughs et al. |

FOREIGN PATENT DOCUMENTS

| | | | |
|---|---|---|---|
| CN | 201662447 U * | 12/2010 | ............... G01K 7/22 |
| CN | 103110410 A | 5/2013 | |
| CN | 103970977 A | 8/2014 | |
| CN | 105116848 A | 12/2015 | |
| CN | 107152757 B * | 9/2017 | ............ A61L 9/015 |
| CN | 108961714 A | 12/2018 | |
| CN | 110009245 A | 7/2019 | |
| CN | 110084928 A | 8/2019 | |
| CN | 110827457 A | 2/2020 | |
| EP | 1669912 A1 | 6/2006 | |
| EP | 2310981 A1 | 4/2011 | |
| JP | 7085166 A | 3/1995 | |
| JP | 11024735 A | 1/1999 | |
| JP | 11317936 A | 11/1999 | |
| JP | 2001356813 A | 12/2001 | |
| JP | 2005242531 A | 9/2005 | |
| JP | 2005311563 A | 11/2005 | |
| KR | 1172747 B1 | 8/2012 | |
| KR | 101445367 B1 | 10/2014 | |
| KR | 1499081 B1 | 3/2015 | |
| WO | 9621264 A3 | 11/1996 | |
| WO | 2004029518 A1 | 4/2004 | |
| WO | 2005045715 A2 | 5/2005 | |
| WO | 2008152433 A1 | 12/2008 | |
| WO | 2008157755 A1 | 12/2008 | |
| WO | 2009012319 A2 | 1/2009 | |
| WO | 2009079648 A1 | 6/2009 | |
| WO | 2010106474 A1 | 9/2010 | |
| WO | 2011025085 A1 | 3/2011 | |
| WO | 2011043732 A1 | 4/2011 | |
| WO | 2011057173 A2 | 5/2011 | |
| WO | 2011123743 A1 | 10/2011 | |

(56) References Cited

FOREIGN PATENT DOCUMENTS

| WO | 2013062725 | A1 | | 5/2013 |
|---|---|---|---|---|
| WO | 2013178819 | A1 | | 12/2013 |
| WO | 2014009291 | A1 | | 1/2014 |
| WO | 2014098861 | A1 | | 6/2014 |
| WO | 2014135517 | A1 | | 9/2014 |
| WO | 2016123536 | A1 | | 8/2016 |
| WO | 2017057274 | A1 | | 4/2017 |
| WO | 2019046580 | A1 | | 3/2019 |
| WO | 2020024553 | A1 | | 2/2020 |
| WO | WO-2021183600 | A1 | * | 9/2021 |

OTHER PUBLICATIONS

Johnson Controls Develops Industry-first AI Driven Digital Solution to Manage Clean Air, Energy, Sustainability, Comfort and Cost in Buildings, 7 pages, 2022. Accessed Aug. 29, 2022.
Johnson Controls and Microsoft Announce Global Collaboration, Launch Integration between Open Blue Digital Twin and Azure Digital Twins, 7 pages, 2022. Accessed Aug. 29, 2022.
Open Blue Companion Desktop User Guide, Johnson Controls, 18 pages, 2022.
Open Blue Digital Twin:Designed for Buildings. Infused with AI, Johnson Controls, 17 pages, 2022. Accessed Aug. 29, 2022.
Open Blue Enterprise Manager User Guide, Johnson Controls, Release 3.1, 72 pages, Jan. 28, 2021.
Open Blue Enterprise Manager User Guide, Johnson Controls, Release 4.0, 78pages, Nov. 29, 2021.
Open Blue Location Manager User Guide, Johnson Controls, Release 2.4.7, 28 pages, Jul. 20, 2022.
Open Blue Enterprise Manager, Optimize Building Portfolio Performance with Advanced Data Analytics and AI, Johnson Controls, 20 pages, Accessed Aug. 29, 2022.
Open Blue Platform, Make Smarter, Faster, More Data-Driven Decisions, Johnson Controls, 15 pages, 2022. Accessed Aug. 29, 2022.
Open Blue, Now, Spaces have Memory and Identity, Johnson Controls, 20 pages, 2022. Accessed Feb. 10, 2022.
Open Blue Enterprise Manager User Guide, Johnson Controls, 108 pages, Release 4.1.3, 2022, Accessed Aug. 29, 2022.
Risbeck et al; "Modeling and Multiobjective Optimization of Indoor Airborne Disease Transmission Risk and Associated Energy Consumption for Building HVAC Systems," Energy and Buildings, vol. 253, 24 pages, 2021.
Sinha et al; "Balance Infection Risk, Sustainability and Comfort with Open Blue," Johnson Controls, 2 pages, 2021.
Olken et al., "Object Lessons Learned from a Distributed System for Remote Building Monitoring and Operation," ACM SIGPLAN Notices, vol. 33, No. 10, pp. 284-295, Oct. 1998.
Proliphix, Inc., "Proliphix IP Devices: HTTP API," 28 pages, Jan. 23, 2006.
Proliphix, Inc., Remote Management User Guide, 12 pages, prior to Aug. 27, 2007.
Richard Rogan et al., "Smart and Final Food Stores: A Case Study in Web Based Energy Information and Collection," Web Based Energy Information and Control Systems: Case Studies and Application, Chapter 6, p. 59-64, 2005.
Sharp, "Actius AL3DU 3D LC Display High Performance 3D Visualization," 2 pages, prior to Mar. 17, 2006.
So et al., "Building Automation on the Information Superhighway," ASHRAE (American Society of Heating Refrigerating, and Air Conditioning) Transactions, vol. 104, Part 2, pp. 176-191, 1998.
So et al., "Building Automation Systems on the Internet," Facilities vol. 15, No. 5/6, pp. 125-133, May/Jun. 1997.
Talon, "Raptor Controller," 6 pages, Oct. 2003.
Talon, "Workstation Software," 4 pages, Nov. 2002.
Trane, "System Programming, Tracer Summit Version 14, BMTW-SVP01D-EN," 623 pages, 2002.
Lucid Design Group, Inc., "Building Dashboard," 2 pages, Printed May 30, 2013.
"America's Largest Managed Security Services Provider Launches Comprehensive, Integrated Covid-19 Safety Program for Office Buildings and Suites," KastleSafeSpaces, 5 pages, May 11, 2020.
"Biometric Door Reader With Body Temperature Detection," Kintronics, 9 pages, accessed May 21, 2020.
"Body Surface Temperature Screening with Alarm Function TVS-200IS/TVS-500IS," Nippon Avionics Co., 3 pages, accessed May 21, 2020.
"BriefCam announces video analytics innovation for contact tracing, physical distancing, occupancy management and face mask detection," BriefCam LTD, 11 pages, Jun. 5, 2020.
"Thermal Imaging SmartPhone Can Be used for Temperature Screening of People," CAT, 3 pages, accessed Jul. 13, 2020.
"Contact Tracing Now Available on Identiv's Hirsch Velocity Access Control Platform," Identiv, 5 pages, May 21, 2020.
Silva et al., "Cough localization for the detection of respiratory diseases in pig houses," ScienceDirect, 7 pages, May 28, 2008.
Oey et al., "Evaluation of Isolation Compliance Using Real Time Video in Critical Care," North Shore University Hospital, 1 page, Oct. 9, 2015.
"Facial Attendace System With Temperature Screening Now in India," IANS, 5 pages, Mar. 19, 2020.
"Plan to Re-Open," Ehigh, 16 pages, accessed Jun. 13, 2020.
"How Smarter AI-Powered Cameras Can Mitigate the Spread of Wuhan Novel," AnyConnect, 22 pages, 2020.
"How to fight COVID-19 with machine learning," DataRevenue, 20 pages, accessed May 25, 2020.
"Inncontrol 5," Honeywell, 2 pages, Aug. 8, 2018.
"IP Door Access Control," Kintronics, 21 pages, 2014.
"Kogniz AI Health Response Platform," Kogniz, 9 pages, accessed May 21, 2020.
"Machine Learning Could Check If You're Social Distancing Properly at Work," MIT Technology Review, 7 pages, Apr. 17, 2020.
Punn et al., "Monitoring COVID-19 social distancing with person detection and tracking via fine-tuned YOLO v3 and Deepsort techniques," 10 pages, May 6, 2020.
"NEC launches dual face biometric and fever detection system for access control," Biometric Update, 4 pages, May 8, 2020.
"Remote temperature monitoring," Axis Communication, 10 pages, 2014.
"FebriEye-AI Based Thermal Temperature Screening System," vehant, 1 pages, 2020.
"See the World in a New Way Hikvision Thermal Cameras," Hikvision, 12 pages, 2017.
Allain, "Trying out the iPhone Infrared Camera: The FLIR One," Wired, 15 pages, 2014.
Dasgupta, "Your voice may be able to tell you if you have Covid," Hindustan Times, 4 pages, Apr. 16, 2020.
Ganguty, "Gurugram-based startup Staqu has modified AI-powered Jarvis to battle coronavirus," Yourstory, 7 pages, Mar. 31, 2020.
Iuliana Bocicor et al. "Wireless Sensor Network based System for the Prevention of Hospital Acquired Infections", arxiv.org, Cornell University Ithaca, NY 14853, May 2, 2017, XP080947042, (Abstract).
Shhedi Zaid Ali et al., "Traditional and ICT Solutions for Preventing the Hospital Acquired Infection", 2015 20th International Conference on Control Systems and Computer Science, IEEE, May 27, 2015, pp. 867-873, XP033188038.
Extended European Search Report, EP application No. 20151295.1, pp. 13, dated May 26, 2020.
U.S. Appl. No. 14/109,496, filed Dec. 17, 2013.
www.geappliances.com/home-energy-manager/about-energy-monitors. htm, "Energy Monitor, Home Energy Monitors, GE Nucleus," 2 pages, printed Jan. 15, 2013.
www.luciddesigngroup.com/network/apps.php#homepage, "Lucid Design Group—Building Dashboard Network—Apps," 7 pages, Jan. 15, 2013.
Preuveneers et al., "Intelligent Widgets for Intuitive Interaction and Coordination in Smart Home Environments," IEEE Eighth International Conference on Intelligent Environments, pp. 157-164, 2012.
Wu et al., "A Web 2.0 Based Scientific Application Framework," 7 pages, prior to Jul. 24, 2014.

(56) References Cited

OTHER PUBLICATIONS

"4.0 Today's Activities, The Home Dashboard," CRBM info@hand website, 46 pages, prior to Apr. 25, 2013.
"Free Facilities Dashboards," eSight Energy Website, 2 pages, prior to Apr. 25, 2013.
Alerton Building Controls, Gallery Prints, 7 pages, Dec. 19, 2013.
Carter, "Industrial Energy Management Dashboards Require a Toolkit," Cross Automation, 11 pages, Nov. 4, 2013.
U.S. Appl. No. 14/169,071, filed Jan. 30, 2014.
U.S. Appl. No. 14/169,083, filed Jan. 30, 2014.
U.S. Appl. No. 14/461,188, filed Aug. 15, 2014.
U.S. Appl. No. 14/482,607, filed Sep. 10, 2014.
e-homecontrols.com, "e-Home Controls Website," link to actual website no longer works, 1 page, prior to Dec. 19, 2013.
http://www.ccbac.com, "C&C (/)—Omniboard," 5 pages, Dec. 19, 2013.
http://www.domcontroller.com/en/, "DomController Home Automation Software—Control Anything from Anywhere," 11 pages, printed Jan. 6, 2015.
http://www.novar.com/ems-bas/opus-building-automation-system, "Novar OPUS BAS," 1 page, prior to Feb. 13, 2013.
Instituto Superior Tecnico, "A 3D Interactive Environment for Automated Building Control," Master's Dissertation, 120 pages, Nov. 2012.
Panduit Corp., "Enable a Building Automation with Panduit Enterprise Solutions," 4 pages, Nov. 2012.
"WEBs-AX Web-Enabled Building Solutions," sales brochure, Honeywell International Inc., Mar. 2009.
"Attune Advisory Services," press release, Honeywell International Inc., Mar. 20, 2012.
EnteliWEB product from Delta Controls, web pages retrieved on May 9, 2013 from http://deltacontrols.com/products/facilities-management/supervisory-software et seq. by the Internet Archive at web.archive.org.
"BACnet Protocol Implementation Conformance Statement" for enteliWEB, Delta Controls, Jul. 17, 2013.
Castle, "7 Software Platforms that Make Building Energy Management Easy," http://greentechadvocates.com/2012/11/28/7-software-platforms-that-make-building-energy-managment-easy/, Nov. 28, 2012.
EnteliWEB catalog sheet, Delta Controls, Inc., 2012.
EnteliWEB catalog sheet, Delta Controls., 2010.
"Intelligent Building Management Systems in Miami," Advanced Control Corp., Mar. 7, 2013.
"The Ohio State University," BACnet International Journal, vol. 5, p. 4, Jan. 2013.
Bobker et al., "Operational Effectiveness in Use of BAS," Proceedings of the 13th International Conference for Enhanced Building Operations, Oct. 8, 2013.
Castelo, "A 3D Interactive Environment for Automated Building Control," Elsevier, Nov. 8, 2012.
"Creston Special Report: How Intelligent building management solutions are reducing operational costs," Creston, 2012.
"Building Automation Software Solutions," Iconics, 2013.
Lacey, "The Top 10 Software Vendors Connecting Smart Buildings to the Smart Grid," http://www.greentechmedia.com/articles/read/the-top-10-companies-in-enterprise-smart-grid, Jul. 18, 2013.
"NiagraAX Product Model Overview," Tridium, Inc., 2005.
"An Overview of NiagraAX: A comprehensive software platform designed to create smart device applications," Tridium, Inc., 2005.
"Phoenix Controls Portal," Phoenix Controls, Inc., 2013.
Quirk, "A Brief History of BIM," Arch Daily, Dec. 7, 2012.
Samad et al., "Leveraging the Web: A Universal Framework for Building Automation," Proceedings of the 2007 American Control Conference, Jul. 11, 2007.
Sinha et al., "9 Key attributes of energy dashboards and analytics tools," https://www.greenbiz.com/blog/2013/08/28/9-key-attributes-energy-dashboards-and=analytics-tools, Aug. 28, 2013.
Sinopoli, "Dashboards for Buildings," http://www/automatedbuildings.com/news/dec10/articles/sinopoli/101119034404sinopoli.html, Dec. 2010.
Sinopoli, "Modeling Building Automation and Control Systems," http://www.automatedbuildings.com/news/jun13/articles/sinopoli/130521122303sinopoli.html, Jun. 2013.
Zito, "What is Tridium Part 1," http://blog.buildingautomationmonthly.com/what-is-tridium/, May 12, 2013.
Zito, "What is Tridium Part 2," http://blog.buildingautomationmonthly.com/tridium-part-2/, Sep. 10, 2013.
Search Report and Written Opinion from related International PCT Application No. PCT/US2018/025189 dated Jul. 17, 2018 (12 pages).
"Data analytics and smart buildings increase comfort and energy efficiency", https://www.microsoft.com/itshowcase/Article/Content/845/Data-analytics-and-smart-buildings-increase-comfort-and-energy-efficiency, Dec. 19, 2016, 8 pages.
Donnelly, "Building Energy Management: Using Data as a Tool", http://www.buildingefficiencyinitiative.org/sites/default/files/legacy/InstituteBE/media/Library/Resources/Existing-Building-Retrofits/Using-Building-Data-as-a-Tool.pdf, Oct. 2012, 9 pages.
"ASHRAE Dashboard Research Project," 29 pages, Aug. 28, 2008.
"Energy Manager User Guide," Release 3.2, Honeywell, 180 pages, 2008.
"Fuzzy Logic Toolbox 2.1, Design and Stimulate Fuzzy Logic Systems," The MathWorks, 2 pages, May 2004.
"Junk Charts, Recycling Chartjunk as junk art," 3 pages, Oct. 2, 2006.
"Model Predictive Control Toolbox 2, Develop Internal Model-Based Controllers for Constrained Multivariable Processes," The MathWorks, 4 pages, Mar. 2005.
Honeywell, "Product Guide 2004," XP-002472407, 127 pages, 2004.
"Statistics Toolbox, for Use with Matlab," User's Guide Version2, The MathWorks, 408 pages, Jan. 1999.
"Vykon Energy Suite Student Guide," Tridium Inc., 307 pages, Mar. 3, 2006.
"Web Based Energy Information Systems for Energy Management and Demand Response in Commercial Buildings," California Energy Commission, 80 pages, Oct. 2003.
Andover Controls, Network News, vol. 2, No. 2, 8 pages, 1997.
Andover Controls World, 4 pages, Spring 1997.
Bell, Michael B. et al., "Early Event Detection-Results from a Prototype Implementation," AICHE Spring National Meeting, 15 pages, Apr. 2005.
Cadgraphics, "The Cadgraphics User's Guide," 198 pages, 2003.
Carrier Comfort Network CCN Web, "Web Browser User Interface to the Carrier Comfort Network," 2 pages, 2002.
Carrier Comfort Network CCN Web, Overview and Configuration Manual, 134 pages, Apr. 2006.
Carrier Comfort Network CCN Web, Product Data, 2 pages, Apr. 2006.
Carrier, "i-Vu Powerful and Intuitive Front End for Building Control," 2 pages, Aug. 2005.
Carrier, "i-Vu Web-Based Integrated Control System," 3 pages, 2005.
Carrier, Demo Screen Shots, 15 pages, prior to Aug. 27, 2007.
Carrier, i-Vu CCN 4.0, Owner's Guide, 20 pages, Jul. 2007.
Carrier, i-Vu CCN, 7 pages, 2007.
Chen, Tony. F., "Rank Revealing QR Factorizations," Linear Algebra and It's Applications, vol. 88-89, p. 67-82, Apr. 1987.
Circon, "i-Browse Web-Based Monitoring and Control for Facility Management," 2 pages, prior to Aug. 27, 2007.
Published Australian Application 2009904740, 28 pages, Application Filed on Sep. 29, 2009.
Echelon, "Energy Control Solutions with the i.Lon SmartServer," 4 pages, 2007.
Echelon, "i.Lon 100e3 Internet Server Models 72101R-300, 72101R-308, 72102R-300, 72103-R300 . . . " 5 pages, copyright 2002-2007.
Echelon, "i.Lon 100e3 Internet Server New Features," 15 pages, Sep. 2006.
Echelon, "i.Lon SmartServer," 5 pages, 2007.
Honeywell News Release, "Honeywell's New Sysnet Facilities Integration System for Boiler Plant and Combustion Safety Processes," 4 pages, Dec. 15, 1995.

(56) References Cited

OTHER PUBLICATIONS

Honeywell, "Excel Building Supervisor-Integrated R7044 and FS90 Ver. 2.0," Operator Manual, 70 pages, Apr. 1995.
Honeywell, "Introduction of the S7350A Honeywell WebPAD Information Appliance," Home and Building Control Bulletin, 2 pages, Aug. 29, 2000; Picture of WebPad Device with touch screen, 1 Page; and screen shots of WebPad Device, 4 pages.
Honeywell, Excel 15B W7760B Building Manager Release 2.02.00, Installation Instructions, 28 pages, Dec. 2004.
Honeywell, The RapidZone Solution, Excel 5000 Open System, Application Guide, 52 pages, Jan. 2004.
http://pueblo.lbl.gov/~olken . . . , "Remote Building Monitoring and Operations Home Page," 5 pages, prior to Aug. 27, 2007.
http://www.commercial.carrier.com/commercial/hvac/productdescription . . . , "Carrier: i-Vu CCN," 1 page, printed Mar. 11, 2008.
http://www.commercial.carrier.com/commercial/hvac/productdescription . . . , "Carrier: 33CSCCNWEB-01 CCN Web Internet Connection to the Carrier Comfort Network," 1 page, printed Mar. 11, 2008.
http://www.docs.hvacpartners.com/idc/groups/public/documents/techlit/gs-controls-ivuccn.rtf, "Products," 5 pages, printed Jul. 3, 2007.
http://www.lightstat.com/products/istat.asp, Lightstat Incorporated, "Internet Programmable Communicating Thermostats," 1 page, printed Mar. 13, 2007.
http://www.sharpsystems.com/products/pc_notebooks/actius/rd/3d/, "Actius RD3D Desktop Replacement Notebook with Industry-Breakthrough 3D Screen," Sharp, 1 page, printed Jun. 16, 2005.
http://www2.sims.berkeley.edu/courses/is213/s06/projects/lightson;final.html, "Lights on a Wireless Lighting Control System," 11 pages, printed Mar. 22, 2007.
I.Lon 100e3 Internet Server, 1 page, prior to Aug. 27, 2007.
I.Lon, SmartServer, 2 pages, prior to Aug. 27, 2007.
I-stat, Demo Screen Shots, 9 pages, printed Mar. 13, 2007.
I-stat, The Internet Programmable Thermostat, 2 pages, prior to Aug. 27, 2007.
Jeffrey Ball, "Green Goal of 'Carbon Neutrality' Hits Limit," TheWall Street Journal, 7 pages, Dec. 30, 2008.
Johnson Controls, Network Integration Engine (NIE) 3 pages, Nov. 9, 2007.
Johnson Controls, Network Integration Engine (NIE), Product Bulletin, pp. 1-11, Jan. 30, 2008.
Kourti, Theodora, "Process Analysis and Abnormal Situation Detection: From Theory to Practice," IEEE Control Systems Magazine, p. 10-25, Oct. 2002.
Mathew, Paul A., "Action-Oriented Benchmarking, Using CEUS Date to Identify and Prioritize Efficiency Opportunities in California Commercial Buildings," 26 pages, Jun. 2007.
Morrison, Don et al., "The Early Event Detection Toolkit," Honeywell Process Solutions, 14 pages, Jan. 2006.
Narang, "Webarc: Control and Monitoring of Building Systems Over the Web," 53 pages, May 1999.
Building Automation System in Michigan, Johnson Heating and Cooling, L.L.C., www.cooljohnson.com/Building-Automation-Systems-Michigan/Macomb-County-Michigan/Building-Automation-Confidential-Customer.html, 4 pages, Accessed Nov. 21, 2022.
Building Automation System Waterford Michigan 48328 JLA, Johnson Heating and Cooling L.L.C., www.cooljohnson.com/Building-Automation-Systems-Michigan/Waterford-Michigan/Building-Automation-System-JLA.html, 3 pages, Accessed Nov. 21, 2022.
Building Automation Systems Waterford Michigan 48330 SJMO, Johnson Heating and Cooling, L.L.C., www.cooljohnson.com/Building-Automation-Systems-Michigan/Waterford-Michigan/Building-Automation-Systems-SJMO.html, 2 pages, Accessed Nov. 21, 2022.
Building Automation Systems Waterford Michigan 48329 WIM, Johnson Heating and Cooling L.L.C., www.cooljohnson.com/Building-Automation-Systems-Michigan/Building-Automation-Systems-WIM.html, 3 pages, accessed Nov. 21, 2022.
Building Automation Clawson Michigan 2.0, Johnson Heating and Cooling L.L.C., www.cooljohnson.com/Building-Automation-Systems-Michigan/Clawson-Michigan/Building-Automation-Clawson-Manor-2.html, 6 pages, Accessed Nov. 21, 2022.
Building Automation in Detroit—Mosaic Christian, Johnson Heating and Cooling L.L.C., www.cooljohnson.com/Building-Automation-Systems-Michigan/Detroit/Mosaic-Christian.html, 5 pages, Accessed Nov. 21, 2022.
Building Automation in Michigan—Divine Grace, Johnson Heating and Cooling L.L.C., www.cooljohnson.com/Building-Automation-Systems-Michigan/Oakland-County-Michigan/Building-Automation-Divine-Grace.html, 3 pages, Accessed Nov. 21, 2022.
Building Automation System Plymouth, Michigan, Johnson Heating and Cooling L.L.C., www.cooljohnson.com/Building-Automation-Systems-Michigan/Plymouth-Michigan/Building-Automation-System-Plymouth-Michigan.html, 8 pages, Accessed Nov. 21, 2022.
Building Automation Systems Shelby Michigan 48316 SG, Johnson Heating and Cooling L.L.C., www.cooljohnson.com/Building-Automation-Systems-Michigan/Shelby-Township-Michigan/Building-Automation-Systems-SG.html, 3 pages, Accessed Nov. 21, 2022.
Building Automation System St. Clair County, Michigan, Johnson Heating and Cooling L.L.C., www.cooljohnson.com/building-Automation-Systems-Michigan/St-Clair-Michigan/Building-Automation-system-St-Clair-Michigan.html, 4 pages, Accessed Nov. 21, 2022.
Building Automation System Troy Michigan Oakland Mall, Johnson Heating and Cooling L.L.C., www.cooljohnson.com/Building-Automation-Systems-Michigan/Troy Michigan/Building-Automation-System-Oakland-Mall.html, 4 pages, Accessed Nov. 21, 2022.
Building Automation System Waterford Michigan 48327 Excel, Johnson Heating and Cooling L.L.C., www.cooljohnson.com/Building-Automation-Systems-Michigan/Waterford-Michigan/Building-Automation-System-excel.html, 2 pages, Accessed Nov. 22, 2022.
Building Automation System Romeo Michigan 48065 RomeoPR, Johnson Heating and Cooling, L.L.C., www.cooljohnson.com/Building-Automation-Systems-Michigan/Romeo-Michigan/Building-Automation-System-RomeoPR.html, 2 pages, Accessed Nov. 21, 2022.
Johnson, Jr., "Cooling Logic™: Changing the Way You Cool," Johnson Solid State, LLC, 12 pages, Nov. 7, 2018.
Building Automation System Clawson Michigan Clawson Manor, Johnson Heating and Cooling L.L.C., www.cooljohnson.com/building-Automation-Systems-michigan/clawson-Michigan/building-Automation-System-Clawson-Manor.html, 3 pages, Accessed Nov. 21, 2022.
Johnson, Jr., "CoolingLogic™ A Method to increase HVAC System Efficiency and Decrease Energy Consumption," A White Paper, Johnson Solid State, L.L.C., 51 pages, Sep. 24, 2016.
Johnson, Jr., "CoolingLogic™: Mosaic Christian Church a Case Study," 140 pages, Feb. 2, 2019.
Title: CoolingLogic a Method to Increase HVAC System Efficiency and Decrease Energy Consumption Author: David L. Johnson Jr. Published online on or about: Sep. 24, 2016 Available online at: CoolingLogic.com Printed copy delivered to Honeywell on Dec. 2, 2016.†
Title: Building Automation System in Michigan Author: David L. Johnson Jr. Published online on or about: Mar. 1, 2017 Available online: www.cooljohnson.com/Building-Automation-Systems-Michigan/Macomb-County-Michigan/Building-Automation-Confidential-Customer.html pp. 4.†

\* cited by examiner
† cited by third party

SYSTEMS AND METHODS FOR REDUCING RISK OF PATHOGEN EXPOSURE WITHIN A SPACE

TECHNICAL FIELD

The present disclosure relates generally to facility management systems, and more particularly to systems and methods for reducing risk of pathogen exposure within a building.

BACKGROUND

Buildings are constructed with a number of different rooms. Each room or zone is often exposed to a different level of occupancy and at different times. To reduce the risk of pathogen exposure to the occupants of the building, it is desirable to disinfected the rooms from time-to-time. This is often a manual process performed by cleaning staff using chemical cleaners. What would be desirable is an unintrusive and data-driven way to track and disinfect spaces within a building.

SUMMARY

The present disclosure relates generally to tracking and disinfection spaces within a building. While a hotel is described as one example application, it will be appreciated that the present disclosure may be used in conjunction with any facility that includes a number of spaces or zones, such as an office building, a hospital, an airport, and/or any other suitable building or facility as desired.

In an example, a system reduces risk of pathogen exposure within a space that is located within a facility having a plurality of spaces that periodically have one or more people within the space. The system includes one or more occupancy sensors that are configured to provide an indication of when the space is occupied and when the space is not occupied. A sanitizer is configured to sanitize surfaces within the space when activated. The sanitizer may be a UV sanitizer that illuminates surfaces in the space and kills pathogens on the surfaces or even in the air. A controller is operably coupled with the one or more occupancy sensors and the sanitizer. The controller is configured to determine a designated time to sanitize the space based at least in part upon information received from the one or more occupancy sensors and to automatically instruct the sanitizer to sanitize surfaces within the space at the designated time.

In another example, a system manages pathogen risk within a guest room within a facility that has a plurality of rentable guest rooms. This can include, for example, a hotel facility, a cruise ship, or any other facility as desired. The system is operably coupled with a Property Management System (PMS) of the facility and includes one or more occupancy sensors that are configured to provide an indication of when the guest room is occupied and when the guest room is not occupied. A sanitizer is configured to sanitize surfaces within the guest room when activated. A controller is operably coupled with the one or more occupancy sensors and the sanitizer. The controller is configured to receive an indication of whether the guest room is rented from the PMS and to receive an indication of whether the guest room is occupied or unoccupied from the one or more occupancy sensors. The controller is configured to determine a designated time to sanitize the guest room based at least in part on whether the guest room is rented or not and/or whether the guest room is occupied or not and to automatically instruct the sanitizer to sanitize surfaces within the guest room at the designated time determined by the controller. In some cases, the designated time may be set when the guest room is not rented and is not occupied.

In another example, a method includes tracking pathogenic safety for a facility that has a plurality of rentable guest rooms, with each of the plurality of guest rooms including one or more air quality sensors and one or more occupancy sensors. An indication of a current air quality within each of the plurality of guest rooms is received at a controller. An indication of current occupancy within each guest room of the plurality of guest rooms is received at the controller. The controller tracks when each guest room of the plurality of guest rooms is due to be sanitized by a sanitizer. The controller communicates with a Property Management System (PMS) of the facility in order to identify when each guest room of the plurality of guest rooms is rented and not rented. The controller automatically activates the respective sanitizer within each guest room when each guest room is due to be sanitized, and is not rented, and is currently unoccupied.

The preceding summary is provided to facilitate an understanding of some of the innovative features unique to the present disclosure and is not intended to be a full description. A full appreciation of the disclosure can be gained by taking the entire specification, claims, figures, and abstract as a whole.

BRIEF DESCRIPTION OF THE FIGURES

The disclosure may be more completely understood in consideration of the following description of various examples in connection with the accompanying drawings, in which.

Figure 1:
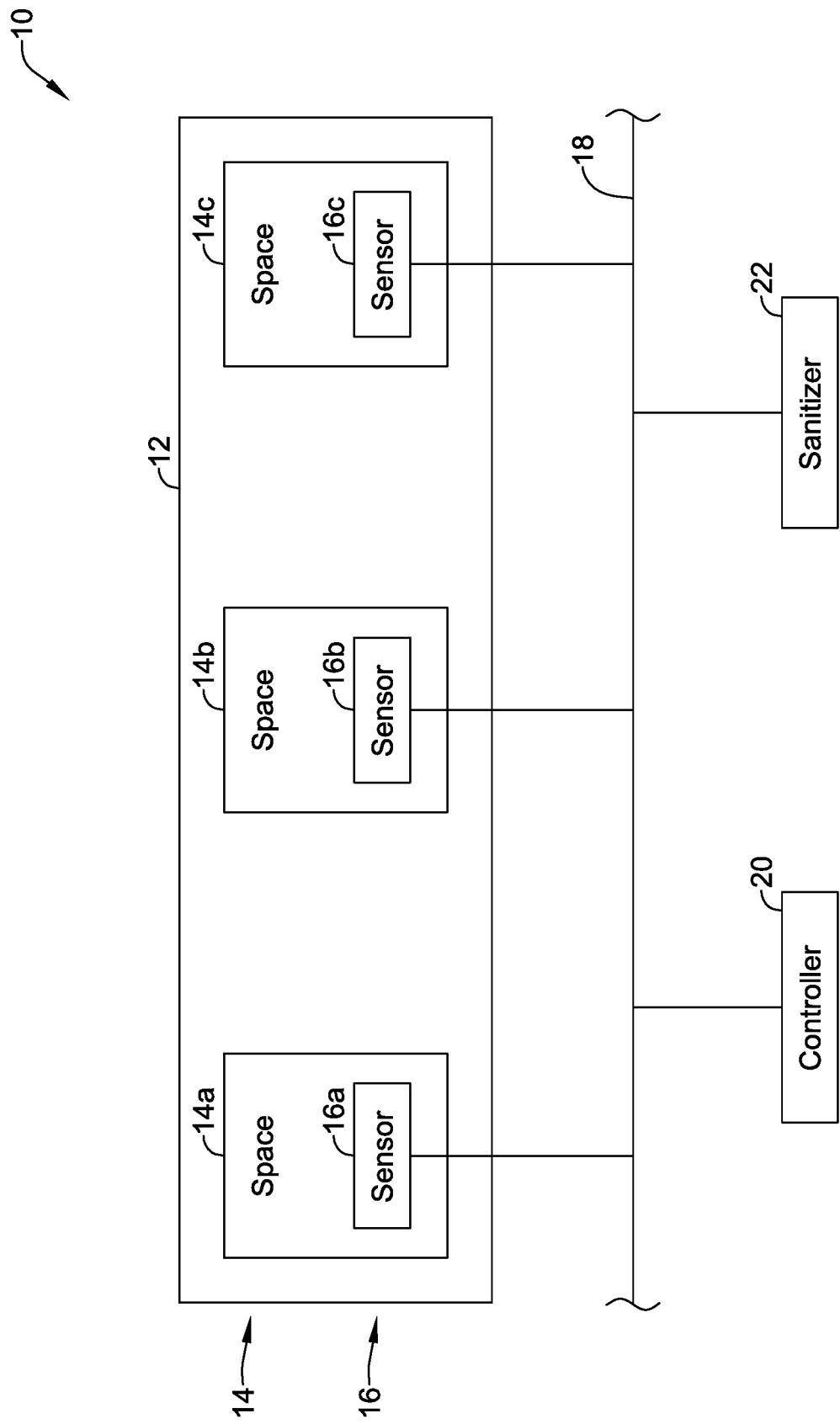
FIG. 1 is a schematic block diagram of an illustrative facility management system.

While the disclosure is amenable to various modifications and alternative forms, specifics thereof have been shown by way of example in the drawings and will be described in detail. It should be understood, however, that the intention is not to limit the disclosure to the particular examples described. On the contrary, the intention is to cover all modifications, equivalents, and alternatives falling within the spirit and scope of the disclosure.

DESCRIPTION

The following description should be read with reference to the drawings, in which like elements in different drawings are numbered in like fashion. The drawings, which are not necessarily to scale, depict examples that are not intended to limit the scope of the disclosure. Although examples are illustrated for the various elements, those skilled in the art will recognize that many of the examples provided have suitable alternatives that may be utilized.

All numbers are herein assumed to be modified by the term "about", unless the content clearly dictates otherwise. The recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular forms "a", "an", and "the" include the plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is contemplated that the feature, structure, or characteristic is described in connection with an embodiment, it is contemplated that the feature, structure, or characteristic may be applied to other embodiments whether or not explicitly described unless clearly stated to the contrary.

FIG. 1 is a schematic block diagram of an illustrative facility management system 10. The illustrative facility management system 10 is installed in a facility 12 and may be considered as being configured to reduce the risk of pathogenic exposure within the facility 12. The facility 12 includes a number of spaces 14 that are individually labeled as 14a, 14b, 14c. It will be appreciated that this is merely illustrative, as the facility 12 will typically include a much greater number of spaces 14 or zones. At least some of the spaces 14 may periodically have one or more people within the space 14. In some cases, the facility 12 may be a hotel, and thus the spaces 14 may be individually rentable guest rooms. The facility 12 may be an office building, or a portion of an office building, and thus the spaces 14 may be individual offices or work spaces. Each space 14 includes one or more sensors 16, although only one sensor 16 is shown in each of the spaces 16. The sensors 16 are individually labeled as 16a, 16b, 16c. The sensors 16 may, for example, be environmental sensors such as temperature sensors, humidity sensors, visible light sensors, UV sensors, particulate matter sensors (e.g. PM2.5), VOC sensors, CO sensors, CO2 sensors, ozone sensors, and/or any other environmental suitable sensor. In some cases, one or more of the sensors 16 may be disposed within a room thermostat within at least some of the spaces 14. Alternatively, or in addition, the sensors 16 may include occupancy sensors such as PIR sensors, mmWave sensors, motion sensors and/or microphones, for example. Some of the sensors 16 may be part of a security system of the facility 12, for example. In some cases, some of the sensors may be video cameras coupled with video analytics.

Each of the spaces 14, and hence the sensors 16 within each of the spaces 14, may be operably coupled with a facility network 18. A controller 20 is operably coupled with the facility network 18 such that the controller 20 is able to receive sensor data from each of the sensors 16 within each of the spaces 14. A sanitizer 22 is also operably coupled to the facility network 18. Accordingly, the controller 20 is operably coupled to both the sensors 16 and the sanitizer 22, through the facility network 18. It is contemplated that the facility network 18 may be a wired, wireless or a combination of wired and wireless.

The sanitizer 22 is configured to be able to sanitize surfaces within a particular space 14 when the sanitizer 22 is actuated within the particular space 14. In some cases, the sanitizer 22 may represent a portable sanitizer that may be manually placed within a particular space 14 when it is time to sanitize the particular space 14. The sanitizer 22 may be configured to move on its own, and thus may be instructed to place itself within a particular space 14. In some cases, the sanitizer 22 may be configured to communicate wirelessly with the controller 20 via the facility network 18.

In some cases, while the sanitizer 22 is shown as being outside of the facility 12, it will be appreciated that the sanitizer 22 may include one or more sanitizing elements that are actually disposed within each of the spaces 14. For example, in some instances, the sanitizer 22 may include one or more ultraviolet (UV) lamps that are disposed within each of the spaces 14. The UV lamps may be part of light fixtures that also include one or more sources of visible light such that the same light fixture can provide visible light and, upon command, UV light in order to sanitize surfaces and/or the air within a particular space 14.

The UV light may produce light that falls within a spectrum of about 100 nanometers (nm) to about 400 nm. This UV light spectrum includes UV-A, which ranges from 315 nm to 400 nm. This UV light spectrum also includes UV-B, which ranges from 280 nm to 315 nm. UV-C, which ranges from 200 nm to 280 nm, is particularly effective for disinfecting. There is also Far-UVC, which ranges from 207 nm to 222 nm and thus is a subset of the UV-C light spectrum. Far-UVC is also particularly effective for disinfecting, and is believed to be safe for human skin and eyes. The UV light spectrum also includes VUV Far-UV, which ranges from 100 nm to 200 nm.

In some cases, the sensors 16 within a particular space 14 may include one or more occupancy sensors that are configured to provide an indication of when the particular space 14 is occupied and when the particular space 14 is not occupied. The controller 20 may be configured to determine a designated time to sanitize the particular space 14 based at least in part upon information received from the sensors 16 (including but not limited to occupancy sensors). The controller 20 may be configured to automatically instruct the sanitizer 22 to sanitize surfaces within the particular space 14 at the designated time. In some cases, the controller 20 may determine the designated time to sanitize the space 14 based upon an indication that the space 14 is currently not occupied and is expected to remain unoccupied for the period of time that will be needed to complete the sanitizing process by the sanitizer 22. For example, to sanitize surfaces in a hotel room using a UV lamp may take some time, such as 5 minutes, 10 minutes, 30 minutes, 1 hour, 2 hours, 3 hours or more, depending on a number of factors such as the intensity of the UV lamp and the distance between the UV lamp and the surfaces to be sanitized.

In one particular example, the particular space 14 represents a hotel room, and the controller 20 may determine that the space 14 is currently empty and is expected to remain empty for a sufficient period of time to complete the sanitizing process based at least in part upon an indication that the space 14 is not rented. In another example, the space 14 may represent an office within an office building, and the controller 20 may determine that the space 14 is currently empty and is expected to remain empty for a sufficient period of time based upon historical occupancy data/patterns for the space 14 that has been learned over time by the controller 20, and/or by a preprogrammed occupancy schedule input by building manager. In some cases, the controller 20 may track occupancy over time in order to ascertain how heavily the space 14 is used, and thus whether the space 14 is in need of sanitizing by the sanitizer. In some cases, the usage of the space must exceed a threshold level of usage before determining that the space is in need of sanitizing. In some instances, the controller 20 may be configured to track the health of the sensors 16 and the sanitizer 22, among other devices, and may provide alerts upon equipment failure (real or imminent).

Figure 2:
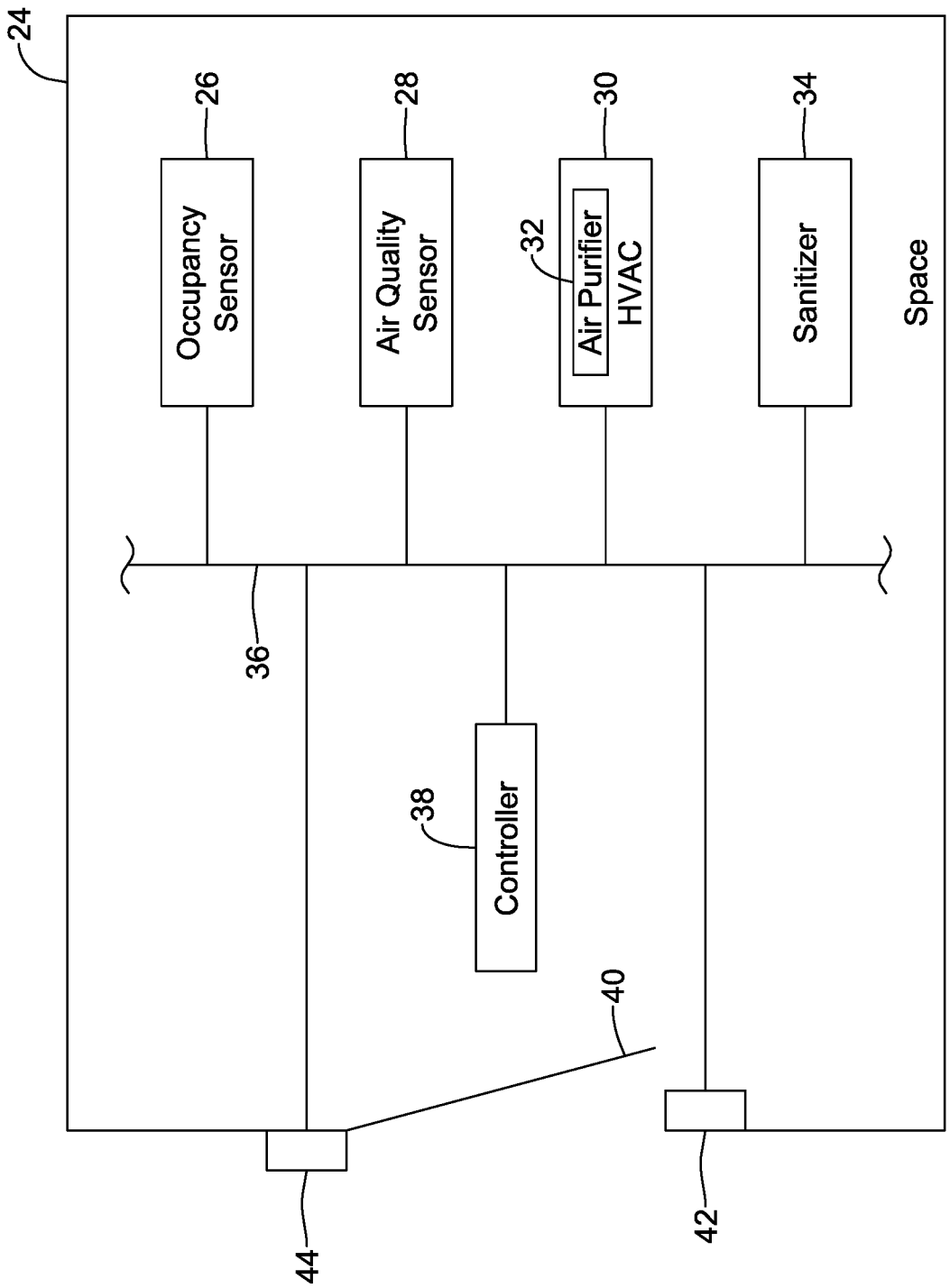
FIG. 2 is a schematic block diagram of an illustrative space within the illustrative facility management system of FIG. 1.

FIG. 2 is a schematic block diagram of an illustrative space 24. The illustrative space 24 may be considered as being an example of the spaces 14, and may represent for example a hotel room, an office, or any other space that is periodically occupied by one or more persons. The space 24 includes an occupancy sensor 26 and an air quality sensor 28. The sensors 26, 28 may be considered as being examples of the sensors 16. The space 24 includes a heating, ventilating and air conditioning (HVAC) system 30 which may include an air purifier 32. The HVAC system 30 may also include a cooling source, a heating source, and a source of fresh air, for example. The air purifier 32 may represent an air filter, for example. An air filter may be a simple filter media, or may be or otherwise include an electrostatic filter element that can be turned on and off as desired. The space 24 includes a sanitizer 34 that is shown as being located within the space 24.

In some cases, it may be useful to periodically sterilize or otherwise clean filters that are within the HVAC system 30, or within ducts bringing conditioned air to the space 24. As the filters filter air, it will be appreciated that the filters can capture bacterial and/or viral material. There is a desire to sanitize the filters by killing these pathogens. A UV-C lamp may be periodically used to kill pathogens trapped within filters. The UV-C lamp may be disposed within the HVAC system 30 or within the aforementioned ducts, for example, and provide UV light to the filter(s) to kill the pathogens on or in the filter(s).

In some cases, the space 24 includes a controller 38 that is operably coupled to a space network 36. The controller 38 may be configured to adjust operation of the HVAC system 30 in response to receiving from the air quality sensor 28 an indication of an air quality that is below a threshold value. The controller 38 may be further configured to activate the air purifier 32 in response to receiving from the air quality sensor 28 an indication of that air quality within the space 24 is below a threshold value.

The sanitizer 34 may be a temporary visitor to the space 24, such as when the sanitizer 34 is a portable sanitizer. The sanitizer 34 may be installed within the space 24, such as being secured to the ceiling of the space 24. Depending on the dimensions and layout of the space 24, the sanitizer 34 may include several different sanitizers 34 located in different portions of the space 24. For example, if the space 24 represents a two bedroom hotel suite with a shared bathroom, there may be one or more sanitizers 34 (e.g. UV Lamps) in each of the two bedrooms, and in the bathroom. An L-shaped office may have several sanitizers 34 disposed in each portion of the "L", for example. This can enable better coverage of the space 24, such that when the sanitizers 34 are activated, all relevant surfaces are sanitized. The sanitizer 34 may provide UV light such as UV-C light that disinfects surfaces that are exposed to the UV-C light for a sufficient period of time.

In some cases, a litmus test device or the like may be placed on a surface of the room before the sanitizer is activated, such as by the cleaning staff after the room is cleaned but before the room is sanitized by the sanitizer. The litmus test device may turn color or change some other characteristic when exposed to the UV-C light for a sufficient period of time. This may confirm to the guest that the room has been sanitized. It is also contemplated that a UV sensor may be placed in the room to monitor the UV lamp. The controller 38 may use the output of the UV sensor to verify that the UV lamp is working properly during sanitization (e.g. UV lamp is not burned out).

The space 24 may be seen as including an entry door 40. In some cases, it can be desirable to provide a warning to others that the sanitizer 34 is currently operating within the space 24 to sanitize surfaces within the space 24. In some cases, some bands of UV light can be considered harmful to humans with sufficient exposure. There may be a desire to be able to stop the sanitizer 34 if someone ignores the warning and opens the entry door 40. In some cases, the space 24 may include a door opening sensor 42 that is configured to provide an indication to the controller 38 that the entry door 40 is open or is being opened. If the space 24 is a hotel room, the door opening sensor 42 may be part of a door lock assembly, such that as a person slides their key card into the door lock assembly, the controller 38 receives notification that the entry door 40 is about to be opened, even before the entry door 40 starts to move. If the space 24 is an office, an office worker swiping their access card at a door lock may have the same effect. The controller 38 is configured to instruct the sanitizer 34 to stop operating when the door opening sensor 42 provides an indication that the entry door 40 is open or will be opened. The space 24 may also include an audio and/or visual indicator 44 that is disposed outside of the space 24 that provides a perceptible warning when the sanitizer 34 is operating in the space 24. In some cases, and as a safety precaution, an emergency "off" switch may be provided in the room that allows someone in the room to immediately turn off the sanitizer. Also, in some cases, a warning light or other warning sign or alarm may be provided inside the room when the sanitizer is running.

The occupancy sensor 26, the air quality sensor 28, the HVAC system 30, the sanitizer 34, the controller 38, the door opening sensor 42, the audio and/or visual indicator 44 and the "off" switch may all be operably coupled with a space network 36 that itself may be coupled with a facility network such as the facility network 18. Some of these network connections may be wired connections such as Ethernet connections. Some of these network connections may be wireless connections, depending on the relative locations of the devices and whether wired connections are possible.

Figure 3:
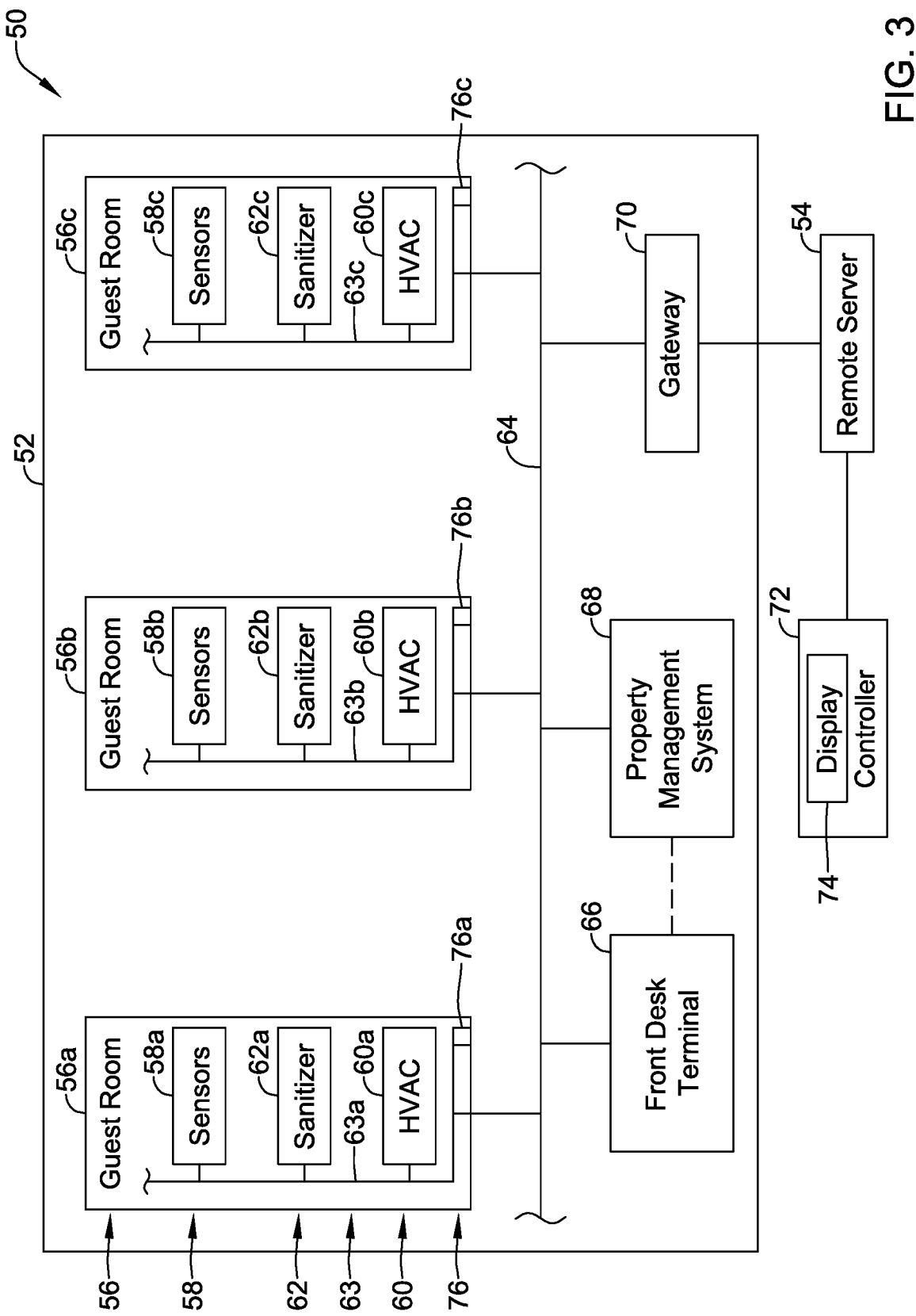
FIG. 3 is a schematic block diagram of an illustrative hotel management system.

FIG. 3 is a schematic block diagram of an illustrative hotel management system 50. The illustrative hotel management system 50 is installed in a hotel 52 and includes a remote server 54 remote from the hotel 52. While the remote server 54 is shown as being exterior to the hotel 52, this is not required in all cases. It is contemplated that the remote server 54 could be disposed within the hotel 52, if desired. The remote server 54 may be a single computer, or the remote server 54 may represent a cloud-based server that includes one or more different computers. The hotel 52 includes a number of guest rooms 56 that are individually labeled as 56a, 56b, 56c. It will be appreciated that this is merely illustrative, as the hotel 52 will typically include a much greater number of guest rooms 56. Each guest room 56 includes one or more sensors 58, although only one sensor 58 is shown per guest room 56. The sensors 58 are individually labeled as 58a, 58b, 58c. The sensors 58 may, for example, be environmental sensors such as temperature sensors, humidity sensors, visible light sensors, UV sensors, particulate matter sensors (e.g. PM2.5), VOC sensors, CO sensors, $CO_2$ sensors, ozone sensors, and/or any other environmental suitable sensor. In some cases, one or more of the sensors 58 may be disposed within a room thermostat within at least some of the guest rooms 56. Alternatively, or in addition, the sensors 58 may include occupancy sensors such as PIR sensors, mmWave sensors, motion sensors and/or microphones, for example. Some of the sensors 58 may be part of a security system of the hotel 52. In some cases, some of the sensors may be video cameras coupled with video analytics.

Each of the guest rooms 56 of the hotel 52 includes a heating, ventilating and air conditioning (HVAC) system 60, individually labeled as 60a, 60b, 60c. The HVAC system 60 in each guest room 56 may be any of a variety of different types of HVAC systems, including split systems. In many cases, the HVAC system 60 in each guest room 56 may be configured to provide warm air, cool air and ambient temperature air circulation as needed, in order to maintain a particular temperature set point within the guest room 56. The particular temperature set point may, for example, include a predetermined temperature set point that is determined for all guest rooms 56 within the hotel 52, particularly for times at which a particular guest room 56 is not rented, or for times at which a particular guest room 56 is rented, but is not occupied. At times in which a particular guest room 56 is both rented and occupied, the temperature set point for that particular guest room 56 may ultimately be determined by the guest, interacting with a room thermostat, for example.

Each of the guest rooms 56 includes a sanitizer 62, individually labeled as 62a, 62b, 62c. The sanitizer 62 may be a temporary visitor to the guest room 56, such as when the sanitizer 62 is a portable sanitizer. The sanitizer 62 may be installed within the guest room 56, such as being secured to the ceiling of the guest room 56. Depending on the dimensions and layout of the guest room 56, the sanitizer 62 may include several different sanitizers 34 located in different portions of the guest room 56. For example, if the guest room 56 is a two bedroom suite with a shared bathroom, there may be one or more sanitizers 62 in each of the two bedrooms, and in the bathroom. An L-shaped guest room 56 may have several sanitizers 62 disposed in each portion of the "L", for example. This can enable better coverage of the guest room 56 such that when the sanitizers 62 are activated, all surfaces are sanitized. The sanitizer 62 may provide UV light such as UV-C light that disinfects surfaces that are contacted by the UV-C light. In some cases, a designated surface may be illuminated with UV light from two or more sides (e.g. the top and bottom). The TV remote and/or other high touch devices may be placed on the designated surface by the cleaning staff.

Each of the guest rooms 56 may include a room network 63, individually labeled as 63a, 63b, 63c. The room network 63 in each guest room 56 may be operably coupled with the sensors 58, the HVAC system 60 and the sanitizer 62 within that guest room 56. The room network 63 in each guest room 56 may be a wired network, such as an Ethernet network, or the room network 63 in each guest room may be a wireless network. Each of the room networks 63 may be considered as being operably coupled with a hotel network 64. Accordingly, data from each guest room 56 can reach the hotel network 64, and thus can be passed on to other devices. Similarly, instructions or other commands from outside the individual guest rooms 56 may be passed to devices within each guest room 56, such as but not limited to the sensors 58, the HVAC systems 60 and the sanitizers 62.

In some cases, the hotel network 64 is also operably coupled to devices that are exterior to the guest rooms 56. For example, the hotel 52 may include a front desk terminal 66. The front desk terminal 66 may, for example, be configured to allow hotel employees to check guests in and out of the hotel 52. While one front desk terminal 66 is shown, it will be appreciated that many hotels 52 may have more than one front desk terminal 66. In some hotels 52, for example, a guest may be able to check themselves out of their guest room 56 using the television in their room. In such cases, the television may be considered as functioning as a terminal, and may replace some of the functionality of the front desk terminal 66. Accordingly, the television in each guest room 56 may also be operably coupled to the hotel network 64.

The illustrative hotel 52 includes a Property Management System (PMS) 68. The PMS 68 may be considered as including software that tracks which guest rooms 56 are rented and which guest rooms 56 are not rented. The PMS 68 may track other parameters and features as well. For example, the PMS 68 may track movie and game rentals within each of the guest rooms 56, so that these rentals can be accounted for and correctly billed to the appropriate room renters. While the PMS 68 is shown as being operably coupled to the hotel network 64, in some cases the PMS 68 may also be coupled with the front desk terminal 66, as indicated in FIG. 3 via a dashed line between the PMS 68 and the front desk terminal 66.

A gateway 70 may provide a connection between the hotel network 64, and hence the various devices operably coupled to the hotel network 64, and the remote server 54. In some cases, the gateway 7 may be as simple as a modem/router that permits the hotel network 64, and the devices on the hotel network 64, to access wide area networks (WAN) such as but not limited to the Internet. The gateway 70 may be configured to allow software to be downloaded to the gateway 70 from the remote server 54. In some cases, the software downloaded to the gateway 70 may provide the gateway 70 with additional functionality. The software downloaded to the gateway 70 may, for example, assist the gateway 70 in communicating with the individual room networks 63 and/or the individual components such as the sensors 58, the HVAC systems 60 and the sanitizers 62 within each of the guest rooms 56. The software downloaded to the gateway 70 may allow the gateway 70 to provide/pass commands to the individual components such as the such as the sensors 58, the HVAC systems 60 and the sanitizers 62 if desired.

The illustrative system 50 includes a controller 72 that is operably coupled to the remote server 54. While shown outside of the hotel 52, in some cases the controller 72 may instead be disposed within the hotel 52. The controller 72 allows an individual to access information available on the hotel network 64. In the example shown, the controller 72 includes a display 74 that may be used to display information. While not illustrated, it will be appreciated that the controller 72 may also include data entry options such as a keyboard, mouse, trackball and the like. The controller 72 may be a lap top computer, a desktop computer, a mobile phone, a tablet computer, and/or any other suitable computing device. In some cases, the remote server 54 and the controller 72 may be one and the same.

In some cases, the sensors 58 within each guest room 56 include one or more occupancy sensors that are configured to provide an indication of when the guest room 56 is occupied and when the guest room 56 is not occupied. The occupancy sensors may include both motion sensors, which can detect movement of people within the guest room 56, but may also include an indication of whether an entry door to the guest room 56 has opened. For example, the door opening sensor 42 shown in FIG. 2 may be used by the controller 72, to determine if a person previously detected via a motion sensor is still in the room, but just sleeping, or has left. In some cases, the one or more sensors may include one or more IR sensors (i.e. thermal sensors) to detect the presence of people and/or animals in a room even when they are not moving (e.g. sleeping).

The controller 72 is configured to receive an indication of whether the guest room 56 is rented from the PMS 68. The controller 72 is configured to receive an indication of whether the guest room 56 is occupied or unoccupied from the one or more occupancy sensors such as the sensors 58. The controller 72 determines a designated time to sanitize the guest room 56 based at least in part on whether the guest room 56 is rented or not and/or whether the guest room 56 is occupied or not. The controller 72 automatically instructs the sanitizer 62 to sanitize surfaces within the guest room 56 at the designated time determined by the controller 72.

While not shown in FIG. 3, it will be appreciated that each guest room 56 may include an outside visual indicator that is disposed outside of the guest room 56, such as the audio and/or visual indicator 44 shown in FIG. 2. The outside visual indicator may be instructed by the controller 72 to display a visual warning outside of the guest room 56 when the sanitizer 62 is operating in the room 56. In some cases, the audio and/or visual indicator 44 may also provide an inside audio and/or visual alert within the guest room 56 to provide a warning inside the guest room 56. The inside and outside audio and/or visual indicator may be activated prior to turning on the sanitizer to give workers and guests a warning that the sanitizer will be activated soon.

Similarly, each guest room 56 includes an entry door such as the entry door 40 and a door sensor such as the door opening sensor 42. The controller 72 may be configured to instruct the sanitizer 62 to turn off when the entry door opens or is open. In some cases, each guest room 56 may include a sanitizer off switch 76, individually labeled as 76a, 76b, 76c. A guest can actuate the sanitizer off switch 76 to provide an instruction via the controller 72 that instructs the sanitizer 62 to turn off.

In some cases, occupancy may be a factor in how frequently a guest room 56 is ventilated, air purified, and/or sanitized. For example, if a particular guest room 56 is not rented, the controller 72 may not ventilate and/or air purify that guest room 56 in order to conserve energy that would otherwise be wasted ventilating and/or air purifying an empty room. The controller 72 may allow that particular guest room 56 to reach an unrented temperature point in order to conserve energy that would otherwise be wasted heating (or cooling) an unrented room that is empty, and is expected to remain empty for a period of time. If the guest room remains un-rented for a time period that is longer than the time that the pathogens can remain alive or active, the sanitizer session may be suspended or terminated.

To help reduce the risk of pathogen exposure further, high touch surfaces within a guest room 56 may be made to be antimicrobial. For example, light switches and light switch covers may be made of or otherwise include an outer layer of a polymer that is rendered antimicrobial. These polymers are known, and can inhibit microbial growth for years. Some polymers, for example, have a 99% plus efficacy even after 15 years. Other plastic surfaces within a guest room 56, such as a telephone, alarm clock, TV remote control and the like may also be made or coated with antimicrobial polymers. In some cases, non-plastic surfaces may be sprayed or otherwise coated with a solution that kills pathogens. Some surfaces may be made of metals that inhibit pathogenic growth, such as but not limited to silver, copper and zinc. As a particular example, silver phosphate glass can be used.

Figure 4:
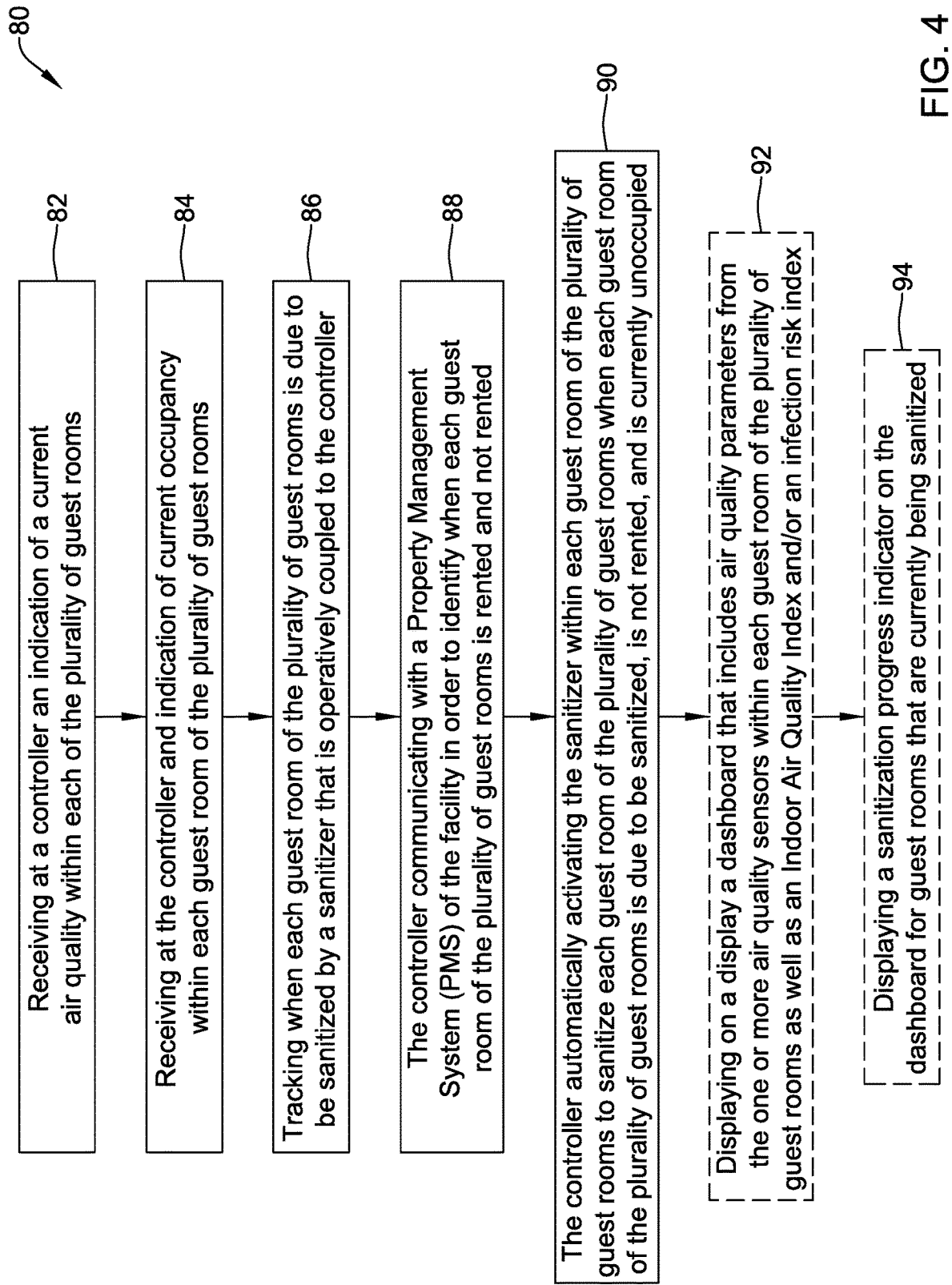
FIG. 4 is a flow diagram showing an illustrative method of tracking pathogenic safety.

FIG. 4 is a flow diagram showing an illustrative method 80 of tracking pathogenic safety for a facility (such as the hotel 52) that has a plurality of rentable guest rooms (such as the guest rooms 56), where each of the plurality of guest rooms includes one or more air quality sensors (such as the air quality sensors 28) and one or more occupancy sensors (such as the occupancy sensors 26). An indication of a current air quality within each of the plurality of guest rooms is received at a controller (such as the controller 72), as indicated at block 82. An indication of current occupancy within each guest room of the plurality of guest rooms is received at the controller, as indicated at block 84. The controller tracks when each guest room of the plurality of guest rooms is due to be sanitized by a sanitizer, as indicated at block 86. The controller communicates with a Property Management System (PMS) of the facility in order to identify when each guest room of the plurality of guest rooms is rented and not rented, as indicated at block 88. The controller automatically activates the sanitizer within each guest room of the plurality of guest rooms to sanitize each guest room of the plurality of guest rooms when each guest room of the plurality of guest rooms is due to be sanitized, and is not rented, and is currently unoccupied, as indicated at block 90.

In some cases, and as optionally indicated at block 92, the controller may be configured to display on a display a dashboard that includes air quality parameters from the one or more air quality sensors within each guest room of the plurality of guest rooms as well as an Indoor Air Quality Index and/or an Infection Risk Index. A sanitization progress indicator may be displayed on the dashboard for guest rooms that are currently being sanitized, as optionally indicated at block 94. The Indoor Air Quality Index may be calculated from a number of air quality parameters such as but not limited to one or more of temperature, humidity, carbon dioxide levels, VOC (volatile organic compounds) levels, particular matter levels as indicated by a PM 2.5 level, and ozone ($O_3$) levels. Ozone may be generated as a result of performing UV sterilization and/or ionization sterilization.

Figure 5:
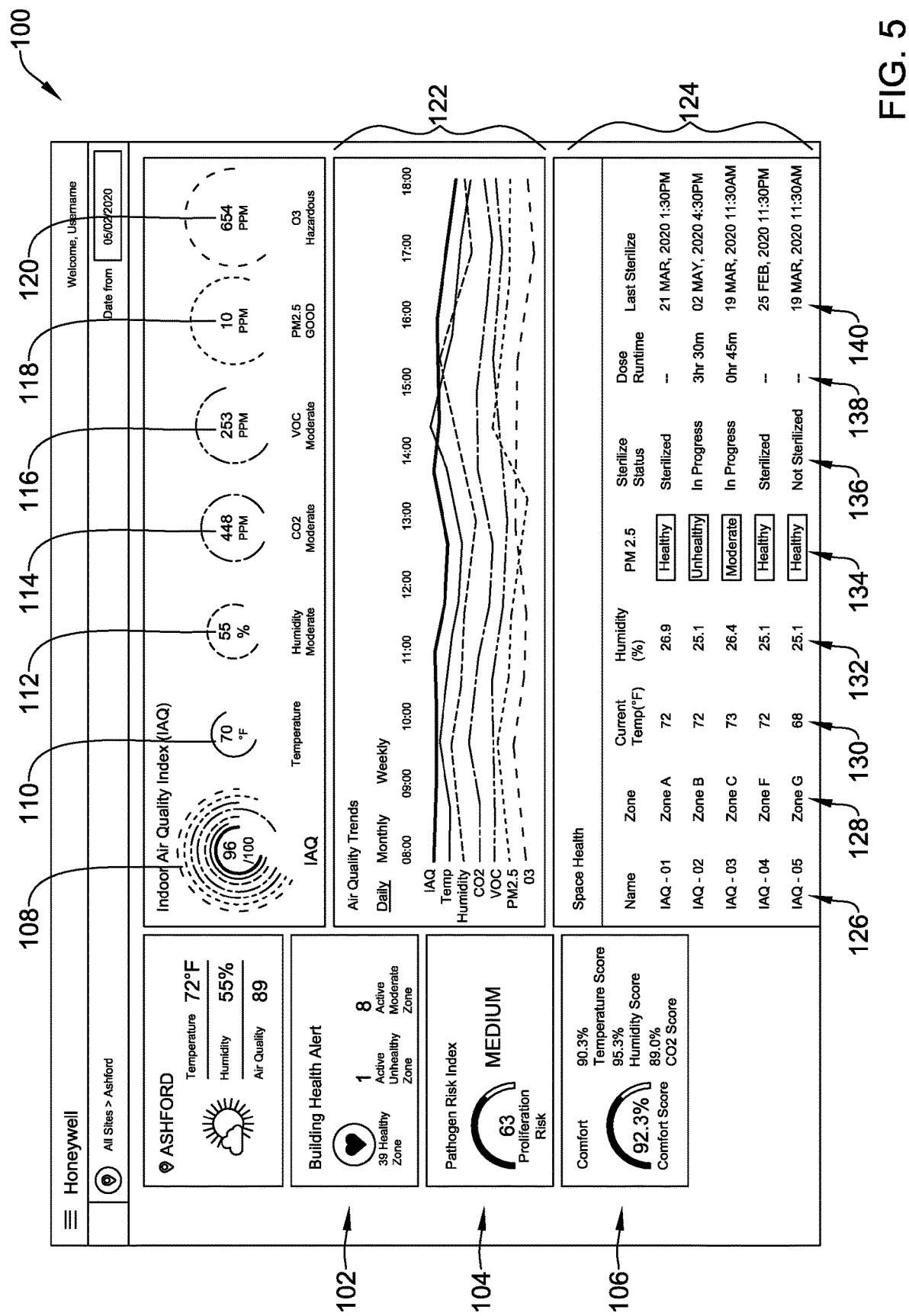
FIG. 5 illustrates a pathogenic-related dashboard.

FIG. 5 is an illustrative dashboard 100 that may be displayed for a facility. The dashboard 100 includes a building health alert 102. As illustrated, the building health alert 102 indicates that there are currently 39 healthy zones, 1 active unhealthy zone and 8 active moderate zones. Active may refer to a zone that is currently being sanitized. An active unhealthy zone is one in which the sanitizing process just began, while an active moderate zone may be one in which the sanitizing process is not yet complete, but has been running for some time. The dashboard 100 also includes an pathogen risk index 104. The pathogen risk index 104, alternatively known as an infection risk index, may be calculated from a number of air quality parameters. For example, particular combinations of temperature and humidity are ideal for pathogenic growth and spread. Such combinations of temperature and humidity would result in a relatively higher pathogen risk index 104 value. Small increases in PM2.5 values can have similar impact on pathogen growth and spread. The dashboard 100 also includes a comfort index 106. Further details regarding the comfort index and how it is calculated may be found in patent applications "Methods and Systems for Evaluating Energy Conservation and Guest Satisfaction in Hotels", now U.S. Pat. No. 11/402,113 and "Methods and Systems for Determining Guest Satisfaction Including Guest Sleep Quality in Hotels, U.S. Publication No. 2022/0044286, both applications are incorporated by reference herein in their entirety.

Across the top, the dashboard 100 includes an Indoor Air Quality Index IAQ icon 108 that is calculated from a number of indoor air quality parameters that are represented by a Temperature icon 110, a Humidity icon 112, a Carbon Dioxide icon 114, a VOC icon 116, a PM2.5 icon 118 and an Ozone icon 120. Each of the icons 110, 112, 114, 116, 118, 120 includes both a numerical value displayed at a center of the icon 110, 112, 114, 116, 118, 120, but also includes a graphical representation in which a portion of a colored circle, with each icon including a unique color. In some cases, a shown, each of these graphical representations is repeated within the IAQ icon 108.

The illustrative dashboard 100 includes a section 122 that shows air quality trends. These may be displayed for any desired period of time, such as but not limited to daily, weekly and monthly. Each of the air quality parameters represented by the icons 110, 112, 114, 116, 118, 120 is repeated within the section 122. The dashboard 100 also includes a Space Health section 124 that shows current conditions within each zone or room. To illustrate, the Space Health section 124 includes a Name column 126, a Zone column 128, a Temperature column 130, a Humidity column 132, a PM2.5 column 134 that displays either Healthy, Unhealthy or Moderate, a Sterilization Status column 136, a Dose Runtime column 138 and a Last Sterilize column 140.

Having thus described several illustrative embodiments of the present disclosure, those of skill in the art will readily appreciate that yet other embodiments may be made and used within the scope of the claims hereto attached. It will be understood, however, that this disclosure is, in many respects, only illustrative. Changes may be made in details, particularly in matters of shape, size, arrangement of parts, and exclusion and order of steps, without exceeding the scope of the disclosure. The disclosure's scope is, of course, defined in the language in which the appended claims are expressed.

What is claimed is:

1. A pathogen risk reduction system for reducing risk of pathogen exposure within a plurality of spaces located within a facility, the facility including an HVAC (Heating, Ventilating and Air Conditioning) system configured to improve air quality within the system, the pathogen risk reduction system comprising:
    a user interface that includes a display;
    a plurality of air quality sensors configured to provide an indication of air quality within each of two or more of the plurality of spaces within the facility;
    a controller operably coupled with the user interface and the plurality of air quality sensors, the controller is configured to:
        receive from each of the plurality of air quality sensors within each of the two or more of the plurality of spaces within the facility a corresponding air quality parameter;
        calculate an indoor air quality index for the facility that is based at least in part on two or more of the plurality of the air quality parameters within two or more of the plurality of spaces within the facility;
        display a dashboard on the display, wherein the dashboard concurrently displays:
            the air quality parameter from each of two or more of the plurality of air quality sensors within each of two or more of the plurality of spaces within the facility;
            the calculated indoor air quality index for the facility displayed in a numerical format; and
            a calculated facility pathogen risk index in a numerical format;
        activate one or more components of the HVAC system of the facility in response to the calculated indoor air quality index for the facility falling below an air quality index threshold; and
        deactivate the one or more components of the HVAC system of the facility in response to the calculated indoor air quality index exceeding the air quality index threshold.

2. The pathogen risk reduction system of claim 1, wherein the pathogen risk index is based at least in part on two or more of the plurality of the air quality parameters.

3. The pathogen risk reduction system of claim 2, wherein the HVAC system includes an air purifier that can be activated, wherein the controller is configured to activate the air purifier when it is determined that the pathogen risk index has exceeded a pathogen risk index threshold.

4. The pathogen risk reduction system of claim 2, wherein the pathogen risk index is based at least in part on a temperature air quality parameter received from a temperature sensor and a humidity air quality parameter received from a humidity sensor.

5. The pathogen risk reduction system of claim 1, wherein the controller is further configured to:
    calculate an indoor air quality index for each of two or more of the spaces within the facility; and
    display the calculated air quality index for each of the two or more of the spaces within the facility.

6. The pathogen risk reduction system of claim 1, wherein the HVAC system includes an air purifier that can be activated, wherein the controller is configured to activate the air purifier when it is determined that the indoor air quality index has fallen below the air quality index threshold.

7. The pathogen risk reduction system of claim 1, wherein the plurality of air quality sensors comprises two or more of a temperature sensor, a humidity sensor, a carbon dioxide sensor, a volatile organic compound sensor, a particulate matter sensor, and an ozone sensor.

8. The pathogen risk reduction system of claim 1, wherein the plurality of air quality sensors comprises a temperature sensor, a humidity sensor, a volatile organic compound sensor and a particulate matter sensor.

9. The pathogen risk reduction system of claim 1, wherein the indoor air quality index is based at least in part on a temperature air quality parameter received from a temperature sensor, a humidity air quality parameter received from a humidity sensor, a volatile organic compound air quality parameter from a volatile organic compound sensor and a particulate matter air quality parameter of a particulate matter sensor.

10. The pathogen risk reduction system of claim 1, wherein the indoor air quality index is based at least in part on a temperature air quality parameter received from a temperature sensor and a humidity air quality parameter received from a humidity sensor.

11. The pathogen risk reduction system of claim 1, wherein the dashboard displays a trend of the indoor air quality index over time.

12. The pathogen risk reduction system of claim 1, wherein the dashboard concurrently displays a trend of two or more of the plurality of air quality parameters over time.

13. A method for reducing risk of pathogen exposure within a plurality of spaces located within a facility, the facility including an HVAC (Heating, Ventilating and Air Conditioning) system, the method comprising:
receiving from each of a plurality of air quality sensors within each of two or more of the plurality of spaces within the facility a corresponding air quality parameter;
calculating a facility pathogen risk index, wherein the facility pathogen risk index is based at least in part on two or more of the plurality of the air quality parameters within each of the two or more of the plurality of spaces within the facility;
displaying a dashboard on a display, wherein the dashboard concurrently displays:
the air quality parameter from each of two or more of the plurality of air quality sensors within each of the two or more of the plurality of spaces within the facility; and
the calculated facility pathogen risk index displayed in a numerical format;
activating one or more components of the HVAC system of the facility in response to the calculated facility pathogen risk index exceeding a pathogen risk index threshold; and
deactivating the one or more components of the HVAC system of the facility in response to the calculated facility pathogen risk index falling below the pathogen risk index threshold.

14. The method of claim 13, further comprising:
activating an air purifier of the HVAC system that services at least one of the plurality of spaces when it is determined that air quality in the corresponding space has fallen below an air quality threshold value.

15. The method of claim 14, further comprising determining that air quality in the space has fallen below an air quality threshold value when the pathogen risk index has exceeded the pathogen risk index threshold.

16. The method of claim 13 further comprising:
calculating an indoor air quality index that is based at least in part on two or more of the plurality of the air quality parameters within each of two or more of the plurality of spaces; and
displaying on the dashboard the calculated indoor air quality index.

17. The method of claim 16 further comprising activating an air purifier of the HVAC system that services at least one of the plurality of spaces when it is determined that indoor air quality index falls below an indoor air quality index threshold.

18. A non-transitory computer readable medium storing instructions thereon that when executed by one or more processors cause the one or more processors to:
receive from each of a plurality of air quality sensors within each of a plurality of spaces within a facility a corresponding air quality parameter;
calculate an indoor air quality index for the facility that is based at least in part on two or more of the plurality of the air quality parameters from each of two or more of the plurality of spaces;
calculate a pathogen risk index for the facility, wherein the pathogen risk index for the facility is based at least in part on two or more of the plurality of the air quality parameters from each of two or more of the plurality of spaces;
display a dashboard on a display, wherein the dashboard concurrently displays:
the air quality parameter from each of two or more of the plurality of air quality sensors from each of two or more of the plurality of spaces;
the calculated indoor air quality index for the facility displayed in a numerical format; and
the calculated pathogen risk index for the facility;
activate one or more components of an HVAC (Heating, Ventilating and Air Conditioning) system of the facility in response to the calculated indoor air quality index falling below an air quality index threshold and/or activate one or more components of the HVAC system of the facility in response to the calculated pathogen risk index exceeding a pathogen risk threshold; and
deactivate the one or more components of the HVAC system of the facility in response to the calculated indoor air quality index exceeding the air quality index threshold and/or deactivate the one or more components of the HVAC system of the facility in response to the calculated pathogen risk index falling below the pathogen risk threshold in order to improve at least one of:
the calculated indoor air quality index for the facility; and
the calculated pathogen risk index for the facility.

19. The non-transitory computer readable medium of claim 18, wherein the instructions stored thereon cause the one or more processors to:
activate an air purifier of the HVAC system that services one or more of the spaces when it is determined that the calculated indoor air quality index for the facility has fallen below the air quality threshold value and/or the pathogen risk index for the facility has exceeded the pathogen risk index threshold.

* * * * *